(12) United States Patent
Schuman et al.

(10) Patent No.: US 6,293,793 B1
(45) Date of Patent: *Sep. 25, 2001

(54) STACKABLE RESERVOIR AND SCALER SYSTEM

(75) Inventors: Robert J. Schuman, Kings Park, NY (US); V. Richard Guilmette, Scotch Plains, NJ (US); Martin I. Septimus, Forest Hills; Alfred E. Corbellini, East Northport, both of NY (US)

(73) Assignee: Dentsply Research & Development Corp., US ( * ) Notice: Subject to any disclaimer, the term of this patent is extended or adjusted under 35 U.S.C. 154(b) by 0 days.

This patent is subject to a terminal disclaimer.

(21) Appl. No.: 09/407,438

(22) Filed: Sep. 29, 1999

Related U.S. Application Data

(63) Continuation of application No. 08/723,199, filed on Sep. 27, 1996, now Pat. No. 6,030,212.

(51) Int. Cl.[7] .................................................. A61C 17/02
(52) U.S. Cl. .............................. 433/86; 433/80; 604/259
(58) Field of Search ................................ 433/80, 82, 84, 433/86, 100, 118; 604/259; D23/207, 208; D24/111

(56) References Cited

U.S. PATENT DOCUMENTS

| Re. 29,687 | 7/1978 | Sertich ...................................... 32/56 |
| Re. 30,536 | 3/1981 | Perdreaux, Jr. ........................ 433/86 |
| D. 216,492 | 1/1970 | Johnson et al. ........................ D83/1 |
| D. 218,241 | 8/1970 | Gilbert et al. ............................ D24/1 |
| D. 308,566 * | 6/1990 | Kapp et al. .......................... D23/208 |
| D. 369,656 | 5/1996 | Vos ...................................... D24/111 |
| D. 422,355 * | 4/2000 | Schuman et al. ..................... D24/111 |
| 2,874,470 | 5/1959 | Richards . |
| 3,075,288 | 1/1963 | Balamuth et al. . |
| 3,077,415 | 2/1963 | Ayres . |
| 3,091,033 | 5/1963 | Ellman . |
| 3,213,537 | 10/1965 | Balamuth et al. . |
| 3,368,280 | 2/1968 | Friedman et al. . |
| 3,375,583 | 4/1968 | Blank et al. . |
| 3,433,226 | 3/1969 | Boyd . |
| 3,488,851 | 1/1970 | Haydu . |
| 3,518,766 | 7/1970 | Burt . |
| 3,526,036 | 9/1970 | Goof . |
| 3,589,012 | 6/1971 | Richman . |
| 3,593,423 | 7/1971 | Jones et al. . |

(List continued on next page.)

FOREIGN PATENT DOCUMENTS

WO 87/04613  8/1987  (WO) .

OTHER PUBLICATIONS

Dentsply/Cavitron CAVI–MED 200 Instruction Manual © 1988. Dentsply International, Inc.
Dentsply CAVI–MED/ProSol; Periodontal Prophylaxis System; Application and Procedure Guidelines No. 3829–N 4/89 30M.

(List continued on next page.)

*Primary Examiner*—Ralph A. Lewis
(74) *Attorney, Agent, or Firm*—Dale R. Lovercheck; James B. Bieber

(57) ABSTRACT

An ultrasonic dental tooth treatment system including an ultrasonic dental handpiece, a fluid reservoir housing and a power control housing. The reservoir housing is supported by the control housing. The reservoir housing encloses two containers which are connected to the selector valve. The selector valve is connected to a control housing conduit which is connected to the handpiece. The control housing encloses a power control circuit which is connected to the handpiece. In a preferred embodiment of the invention a fluid dispenser includes at least one readily removable reservoir container supported by a reservoir housing having a pivotable cover and a fluid control valve. The cover is pivotable between an open position and a closed position. The valve is closed by the cover when the cover is in its open position.

17 Claims, 27 Drawing Sheets

U.S. PATENT DOCUMENTS

| | | | |
|---|---|---|---|
| 3,593,425 | 7/1971 | Robinson . | |
| 3,631,631 | 1/1972 | Greenstein . | |
| 3,636,947 | 1/1972 | Balamuth . | |
| 3,645,255 | 2/1972 | Robinson . | |
| 3,654,502 | 4/1972 | Carmona et al. . | |
| 3,693,613 | 9/1972 | Kelman . | |
| 3,703,037 | 11/1972 | Robinson . | |
| 3,718,973 | 3/1973 | Slater et al. . | |
| 3,760,799 | 9/1973 | Crowson . | |
| 3,807,048 | 4/1974 | Malmin . | |
| 3,809,977 | 5/1974 | Balamuth et al. . | |
| 3,858,358 | 1/1975 | Stachowiak et al. . | |
| 3,863,628 | 2/1975 | Vit . | |
| 3,864,472 | 2/1975 | Pensak et al. . | |
| 3,882,638 | 5/1975 | Black . | |
| 3,887,701 | 6/1975 | Nachtigal . | |
| 3,924,335 | 12/1975 | Balamuth et al. . | |
| 3,924,806 | 12/1975 | Schowiak . | |
| 3,930,173 | 12/1975 | Banko . | |
| 3,956,826 | 5/1976 | Preadreaux, Jr. . | |
| 3,972,123 | 8/1976 | Black . | |
| 3,976,222 | 8/1976 | Spagnolo . | |
| 4,012,842 | 3/1977 | Vit . | |
| 4,051,337 | 9/1977 | Warrin . | |
| 4,116,239 | 9/1978 | Ewen . | |
| 4,148,309 | 4/1979 | Reibel . | |
| 4,160,821 | 7/1979 | Sipos . | |
| 4,162,576 | 7/1979 | Takemoto et al. . | |
| 4,184,064 | 1/1980 | Williams . | |
| 4,193,196 | 3/1980 | Kuris et al. | 433/82 |
| 4,193,197 | 3/1980 | Kuris et al. | 433/82 |
| 4,215,476 * | 8/1980 | Armstrong | 433/80 |
| 4,247,288 | 1/1981 | Yoshii et al. | 433/224 |
| 4,248,379 | 2/1981 | Hollstein et al. . | |
| 4,249,901 | 2/1981 | Wieser | 433/119 |
| 4,260,380 | 4/1981 | Nash | 433/119 |
| 4,276,024 | 6/1981 | Warrin | 433/99 |
| 4,276,880 | 7/1981 | Malmin . | |
| 4,283,174 | 8/1981 | Sertich | 433/119 |
| 4,283,175 | 8/1981 | Nash | 433/119 |
| 4,291,017 | 9/1981 | Beierle et al. | 424/52 |
| 4,295,827 | 10/1981 | Martin et al. | 433/81 |
| 4,302,186 | 11/1981 | Cammack et al. | 433/80 |
| 4,302,481 | 11/1981 | Ribnitz et al. | 427/27 |
| 4,315,742 | 2/1982 | Nash et al. | 433/86 |
| 4,330,278 | 5/1982 | Martin | 433/81 |
| 4,332,558 | 6/1982 | Lustig | 433/86 |
| 4,339,432 | 7/1982 | Ritchey et al. | 424/54 |
| 4,370,131 | 1/1983 | Banko | 433/86 |
| 4,428,748 | 1/1984 | Peyman et al. | 604/22 |
| 4,453,919 | 6/1984 | Takeshita | 433/120 |
| 4,472,373 | 9/1984 | Ryan | 424/54 |
| 4,487,582 | 12/1984 | Warrin | 433/88 |
| 4,490,114 | 12/1984 | Kleesattel et al. | 433/105 |
| 4,492,574 | 1/1985 | Warrin et al. | 433/81 |
| 4,505,676 | 3/1985 | Gonser | 433/119 |
| 4,522,806 | 6/1985 | Mulhemann et al. | 424/52 |
| 4,582,702 | 4/1986 | Grollier | 424/52 |
| 4,592,728 | 6/1986 | Davis | 433/80 |
| 4,601,900 | 7/1986 | Noponen et al. | 424/54 |
| 4,644,937 | 2/1987 | Hommann | 128/66 |
| 4,682,949 | 7/1987 | Warrin | 433/81 |
| 4,731,019 | 3/1988 | Martin | 433/119 |
| 4,770,632 | 9/1988 | Ryder et al. | 433/28 |
| 4,820,152 | 4/1989 | Warrin et al. | 433/86 |
| 4,850,868 | 7/1989 | Wright et al. | 433/116 |
| 5,060,825 | 10/1991 | Palmer et al. | 222/25 |
| 5,087,198 | 2/1992 | Castellini | 433/80 |
| 5,125,837 | 6/1992 | Warrin et al. | 433/98 |
| 5,199,604 | 4/1993 | Palmer et al. | 222/25 |
| 5,344,317 | 9/1994 | Pacher et al. | 433/85 |
| 5,419,703 | 5/1995 | Warrin et al. | 433/216 |
| 5,478,236 | 12/1995 | Annunzio | 433/98 |
| 6,030,212 * | 2/2000 | Schuman et al. | 433/80 |

OTHER PUBLICATIONS

Dentsply/Equipment Division; Instruction Manual; Dentsply/Cavitron Model 3000; Ultrasonic Unit © 1987, Dentsply International, Inc.

Alrich/Girard, Inc., Redford, MI (No Date) Brochure.

Bair et al in Periodontal Case Reports, vol. 7, Nov. 1, 1985; Method for Altering the Periodontal Pocket Environment from Anaerobic to Aerobic.

* cited by examiner

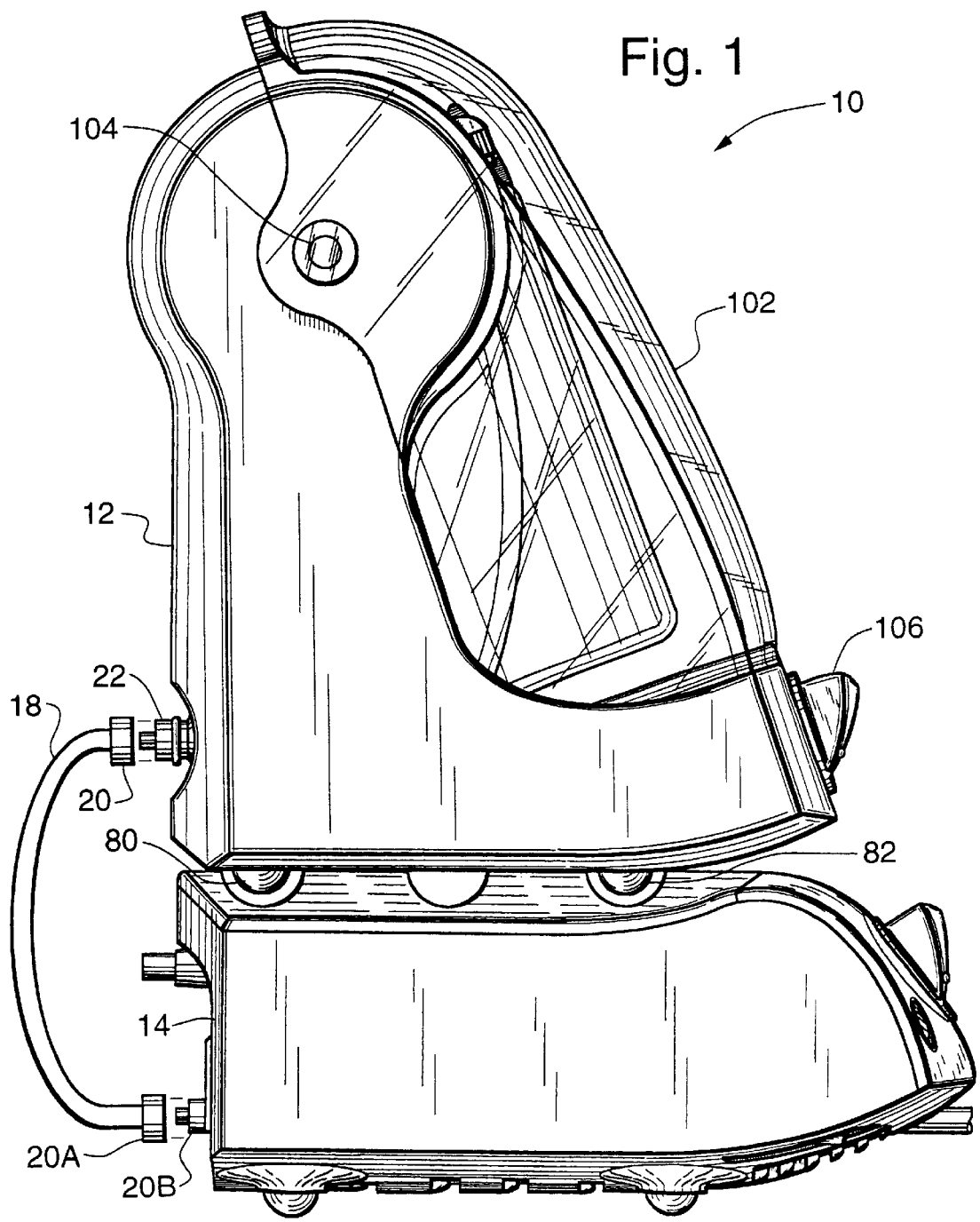

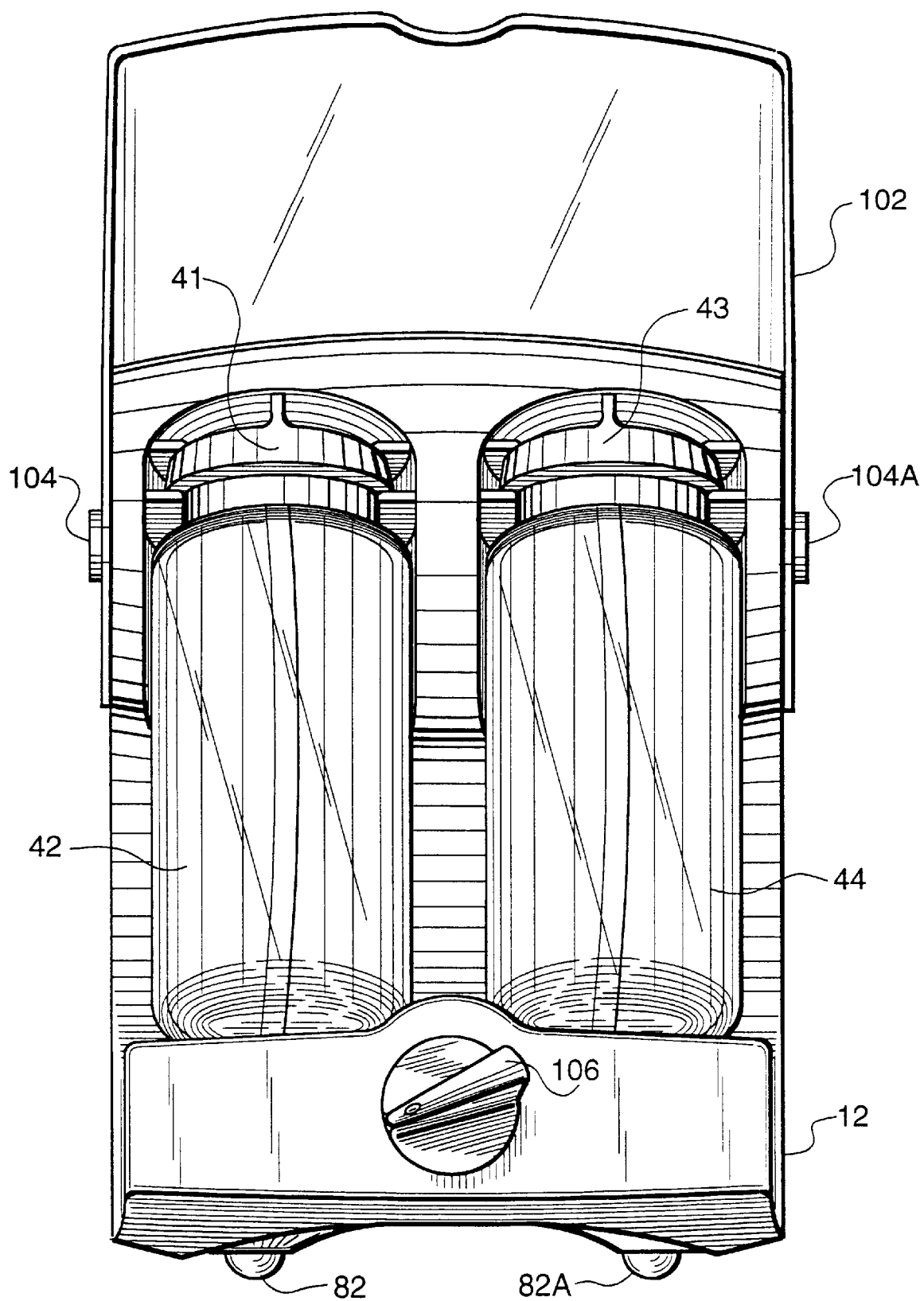

STACKABLE RESERVOIR AND SCALER SYSTEM

This application is a continuation of application Ser. No. 08/723,199, filed Sep. 27, 1996 now U.S. Pat. No. 6,030,212.

The invention relates to dental scaling systems. The invention provides a stacking dental reservoir and scaling system. The present invention provides a reservoir housing having at least one container which is readily connected to a power control housing and stackable thereon. The level of liquid in each container in the reservoir housing is readily visually inspected through a clear plastic (polymeric) cover. The cover pivots on hinges to swing the lower end of the cover above the reservoir housing to open the housing for removal and/or installation of containers.

It is an object of the invention to provide an ultrasonic dental tooth treatment system including an ultrasonic dental handpiece and attaching cable assembly and control housing and a fluid reservoir housing which encloses two containers, each connected to a selector valve connected to a control housing conduit connected to a handpiece conduit.

It is an object of the invention to provide a fluid dispenser which includes readily removable reservoir supported by a reservoir housing having a cover which is pivotable between an open position and a closed position and an interlock valve which is closed by the cover when the cover is in its open position.

It is an object of the invention to provide a stacking dental reservoir and scaling system.

It is an object of the invention to provide a dental scaler system having a reservoir housing with a clear plastic cover which pivots on hinges to swing the lower end of the cover above the reservoir housing to open the housing for the removal and/or installation of containers, as is provided by the present invention.

It is an object of the invention to provide a stackable reservoir housing having a self contained three position selector valve connected in fluid flow communication to a source of air pressure for dispensing from either of two reservoir liquid containers or from a water supply through the selector valve. In a preferred embodiment of the invention only fluid from any one of the containers is conveyed to the handpiece and the system is not connected to an external water supply. By so doing the system can dispense clean water. The system can also be connected to an external water supply, which can also be dispensed to a scaler system.

Warrin et al in U.S. Pat. No. 5,419,703 discloses a method of subgingival scaling and lavage. The apparatus disclosed in Warrin et al includes reservoirs for storing medicament inside a base unit.

The invention solves the problems of the prior art fluid dispensing dental system.

BRIEF DESCRIPTION OF THE DRAWINGS

FIG. 1 is a side view of the right side of a stackable reservoir housing stacked upon a scaler housing in accordance with the invention.

FIG. 8 is a front view of a stackable reservoir housing shown in FIGS. 1–9 with its lid in open position.

BRIEF DESCRIPTION OF THE INVENTION

An ultrasonic dental tooth treatment system including an ultrasonic dental handpiece, a fluid reservoir housing and a power control housing. The reservoir housing is supported by the control housing. The reservoir housing encloses two containers having input passages which are connected to the air pressurization and venting distribution selector valve. The container has output passages which are connected to a control housing conduit which is connected through a solenoid valve and flow control device to the handpiece. The control housing encloses a power generating (and/or control) circuit which is connected to the handpiece. In a preferred embodiment of the invention a fluid dispenser includes a readily removable reservoir supported by a reservoir housing having a pivotable cover and a cover actuated fluid (pressurized air) interlock fluid control valve. The cover is pivotable between an open position and a closed position. The cover actuated interlock valve is closed by the cover when the cover is in its open position. The cover actuated interlock valve is in open position when the cover is in closed position.

A fluid dispenser includes a readily removable container of the invention supported by a reservoir housing having housing fluid flow connectors (or couplings) a pivotable cover and an air pressure venting distribution fluid selector control valve. The container has a cap with a fluid and an air flow connector (or port). The housing connectors (or couplings) are connected to the cap connectors (or ports). Air pressure is supplied through one coupling to the reservoir and fluid exits from the same reservoir through another coupling. The seals on the coupling are so placed that upon removal of a reservoir, the seal on the air supply coupling disengages before the seal on the liquid coupling, thereby further venting the air pressure from the reservoir, and preventing leakage during disengagement of the reservoirs. The cover is pivotable between an open position and a closed position. An interlock valve is closed by the cover when the cover is in the open position thereby venting reservoir pressure and at the same time preventing air pressure from entering the reservoirs. The valve is open when the cover is in closed position. The cover in closed position prevents the cap from moving sufficiently for the cap connector to disengage from the housing connector.

The position at the pivots, about which the cover rotates, is located below the contact point between the container caps and the cover. When either container is pressurized the force of the container cap against the cover thereby causes the cover to be forced into a closed position.

DETAILED DESCRIPTION OF THE INVENTION

Figure 14:
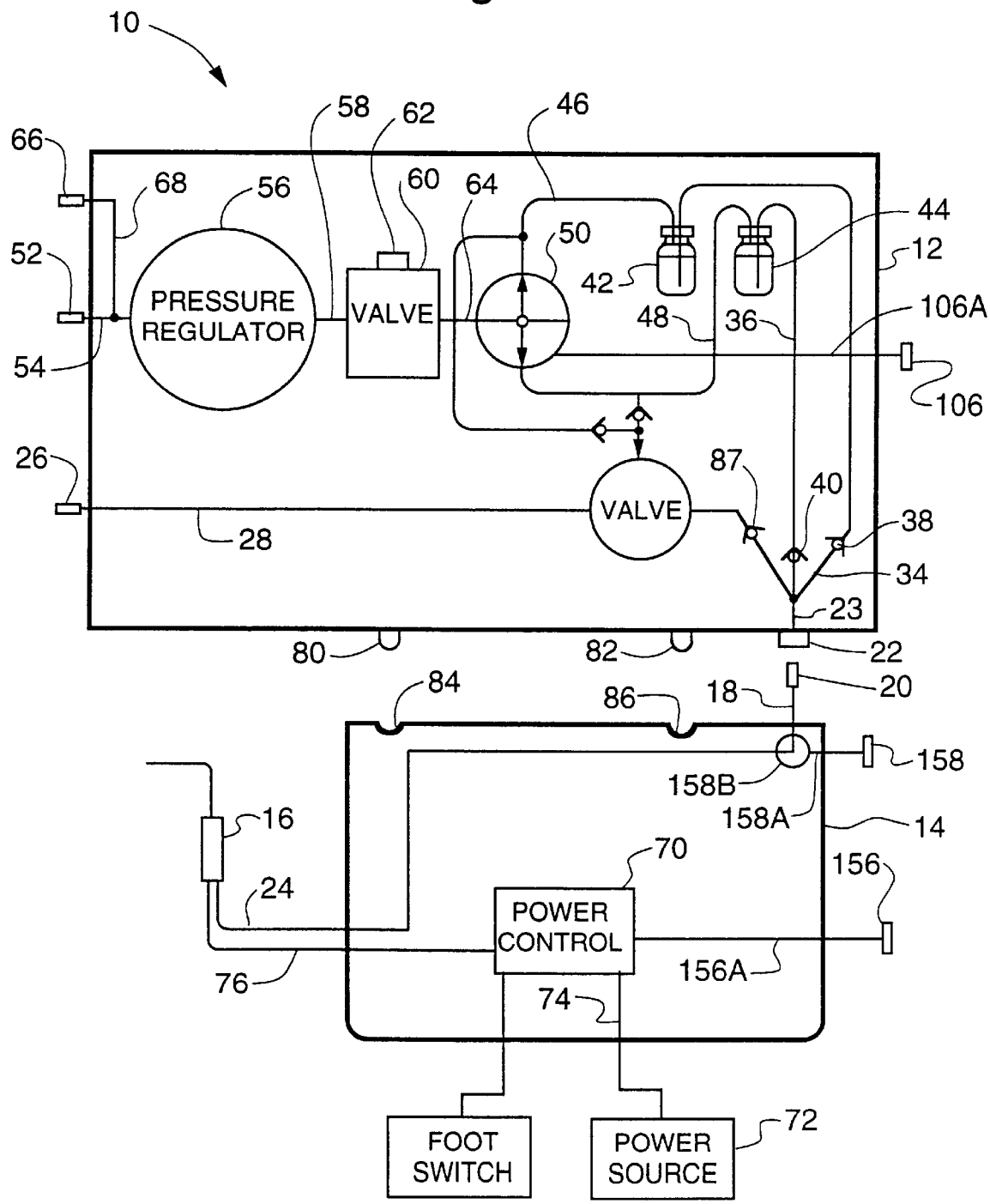
FIG. 14 is schematic diagram of the stacking dental reservoir and scaling system shown in FIGS. 1, 1A and 1B.

The invention is now described with more particular reference to FIGS. 1–19. It is seen that stacking dental reservoir and scaler system 10 includes a reservoir housing 12 and a scaler housing 14 and a handpiece 16 as shown in FIGS. 1 and 14. The scaler housing 14 is connected through fluid conveying conduit 18 to coupler 20 which has a shut-off valve. Coupler 20 is inserted in fluid type connection into coupler 22 which has a shut-off valve. Coupler 22 connects fluid conveying conduit 23 to conduit 18. Conduit 18 is connected by couplers 20A and 20B through solenoid valve and flow control device to conduit 24 to convey fluid into ultrasonic handpiece 16.

Coupler with automatic shut-off valve 26 is adapted to be connected to a water supply, which preferably has a pressure of at least 10 psig. Preferably, the water supply has a pressure of at least 20 psig. More preferably the water supply has the pressure of about 60 psig. Water is conveyed from the water supply through the coupler and shut off valve 26 through conduit 28 to air pilot valve 30. Water is conveyed from air pilot valve 30 through conduit 32 into conduit 23, and conduit 18 through a solenoid valve and flow control device into conduit 24 and into handpiece 16. Conduits 34 and 36 have check valves 38 and 40 respectively and are connected to reservoir containers 42 and 44 respectively. Containers 42 and 44 have caps 41 and 43 respectively. Conduit 32 has check valve 87 and is connected to air pilot valve 30.

Reservoir containers 42 and 44 are connected through conduits 46 and 48 respectively to venting distribution selector valve 50. Coupler 52, which has an automatic shut-off valve, is connected to an air supply of pressurized air, which preferably is regulated to have an air pressure of about 100 psig. Coupler 52 is connected through conduit 54 to pressure regulator 56. Pressure regulator 56 is connected through conduit 58 through interlock valve 60. Valve 60 has a button 62 which must be pressed to open valve 60. When button 62 is pressed, air is conveyed through valve 60 through conduit 64 to selector valve 50. Coupler 66 which has an automatic shut-off valve is connected to conduit 68. Conduit 68 is connected to conduit 54. Coupler 66 provides a connection to pressurized air to operate other devices.

Power control (or generator) 70 is connected to power source 72 through electrical conductor 74 and to power control 70. Power control (or generator) 70 is connected to handpiece 16 through electrical conductor 76.

Feet 80, 80A, 82 and 82A are connected to bottom wall 80B of reservoir housing 12. Feet 80, 80A, 82 and 82A are supported in grooves 84 and 86 in the upper face of scaler housing 14. Feet 80 and 82 are connected to the bottom of the reservoir housing 12.

Reservoir housing 12 has a cover 102 which is opened by pivoting around hinge 104 and 104A. Knob 106 is connected by selector valve stem 106A to valve 50. Turning knob 106 to one side positions the valve 50 to convey fluid from one reservoir through conduit 18. Turn the knob 106 in the other direction from center positions valve 50 to convey fluid from the other reservoir through conduit 18 by pressurization of the respective reservoir chamber. Turning knob 106 to center position vents air from air pilot valve, causing air pilot valve to open and thereby causing external water through conduit 18.

Feet 80 and 80A are supported on groove 160 of scaler housing 14. Feet 82 and 82A are supported in groove 164 in the upper surface of scaler housing 14. Grooves 160 and 164 prevent feet 80, 80A, 82 and 82A from slipping in forward or reversed directions which are perpendicular to the central axis of the groove. Groove 162 is also provided in the upper surface of scaler housing 14. Grooves 160, 162 and 164 are also adapted for placement of handpiece 16 when reservoir housing 12 is not stacked upon scaler housing 14. Holder 170 is adapted to hold handpiece 16. Holder 170 is connected to scaler housing 14. Knob 158 is connected by valve stem 158A to fluid flow control valve 158B. Knob 156 is connected by electrical conductor 156A to power control 70.

Figure 1A:
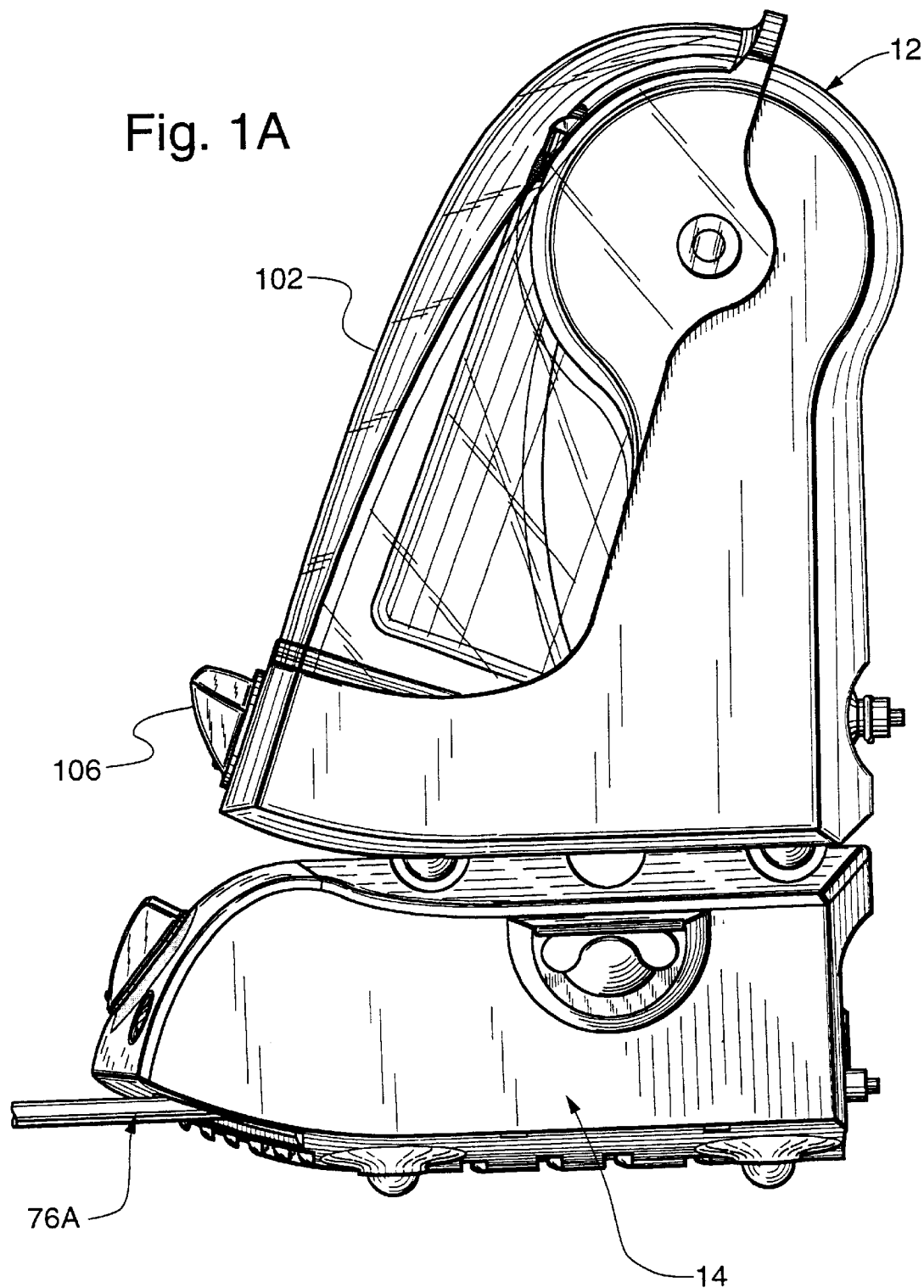
FIG. 1A is a side view of the left side of the stackable reservoir housing stacked upon a scaler housing shown in FIG. 1.
Figure 7:
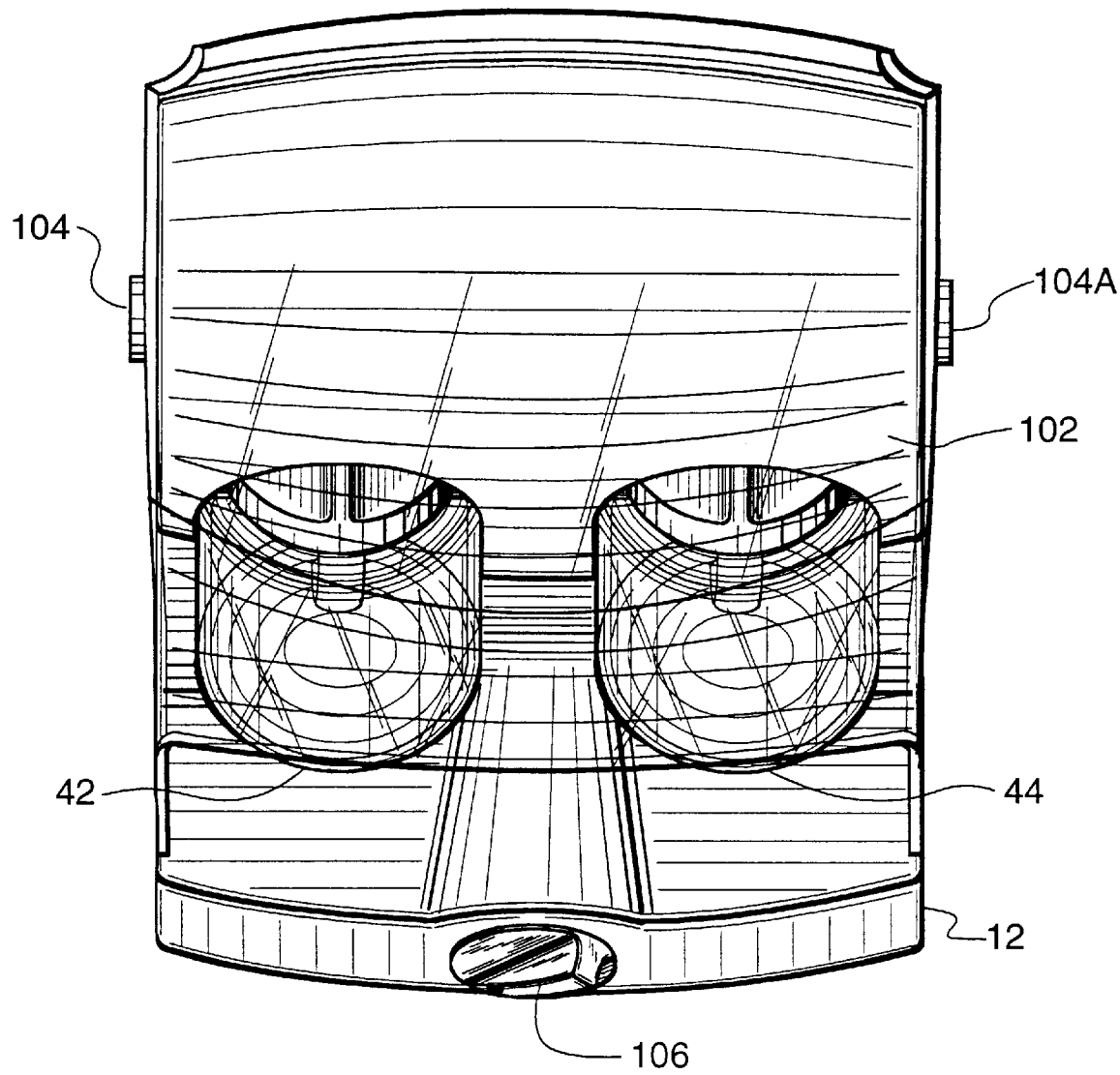
FIG. 7 is a top view of a stackable reservoir housing shown in FIGS. 1–9 with its lid in open position.
Figure 7A:
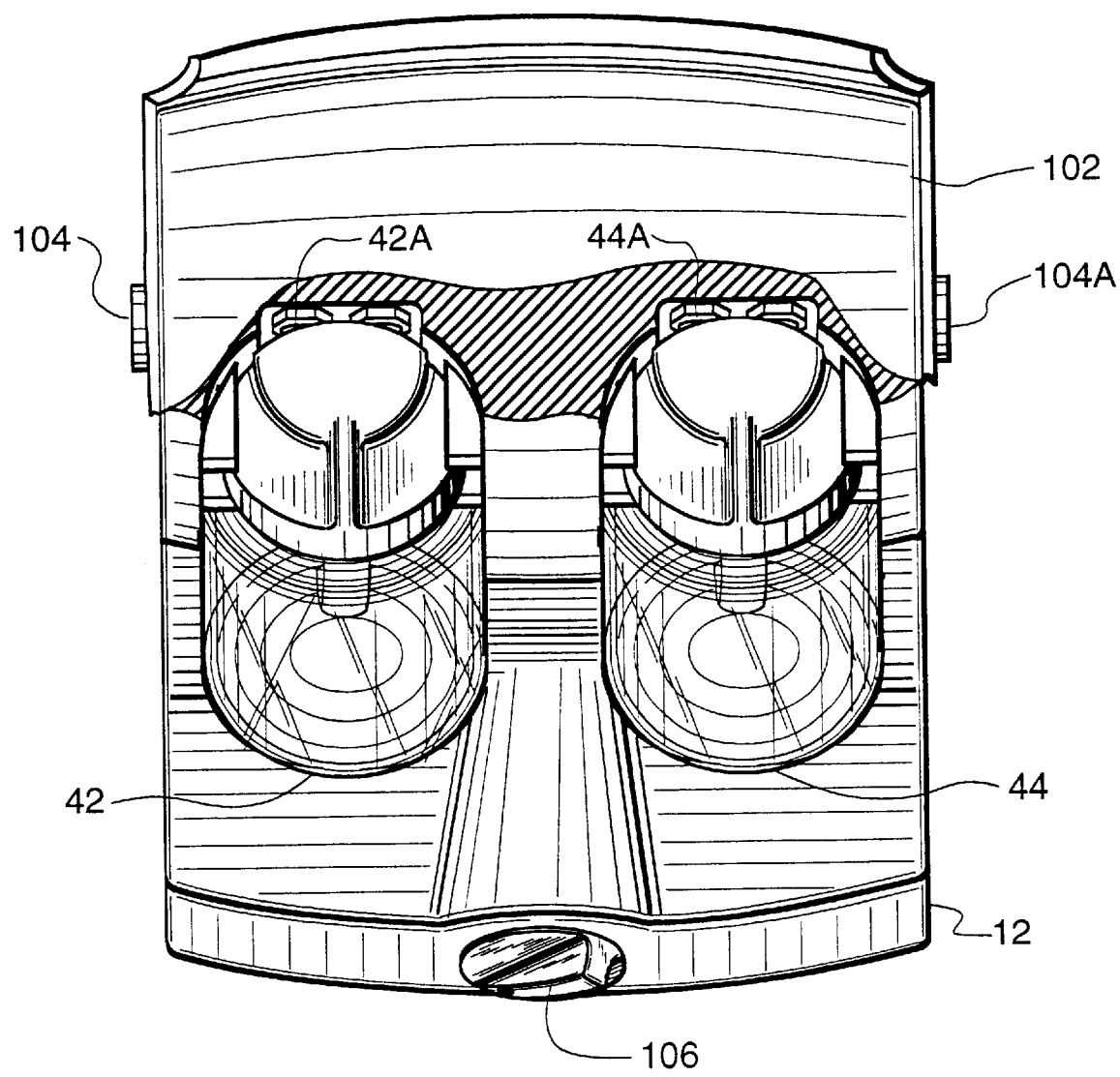
FIG. 7A is a top view of a stackable reservoir housing shown in FIGS. 1–9 with its lid in open position with the lid partially cut away.
Figure 9:
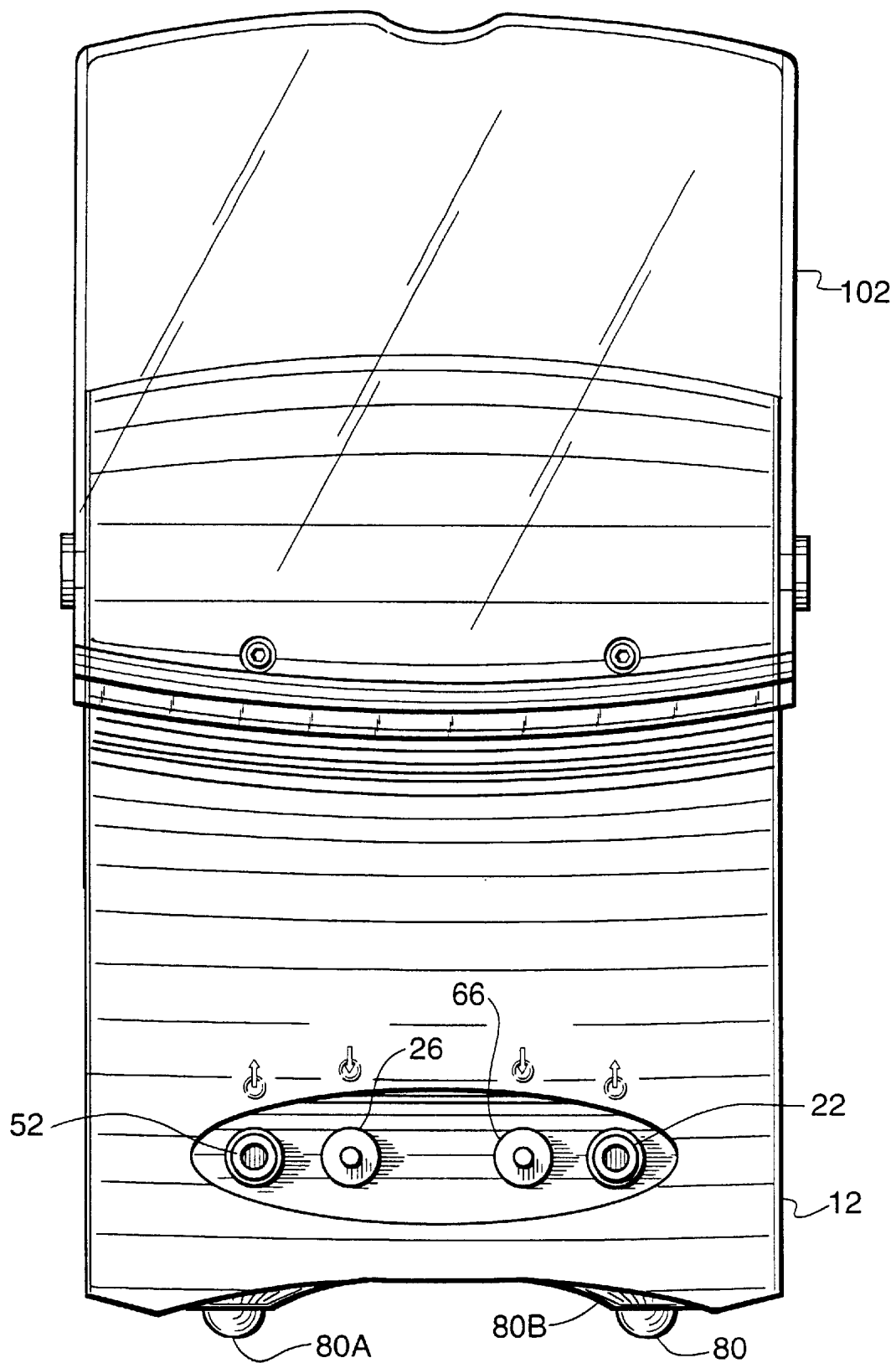
FIG. 9 is a rear view of the stackable reservoir housing shown in FIGS. 1–9 with its lid in open position.
Figure 10:
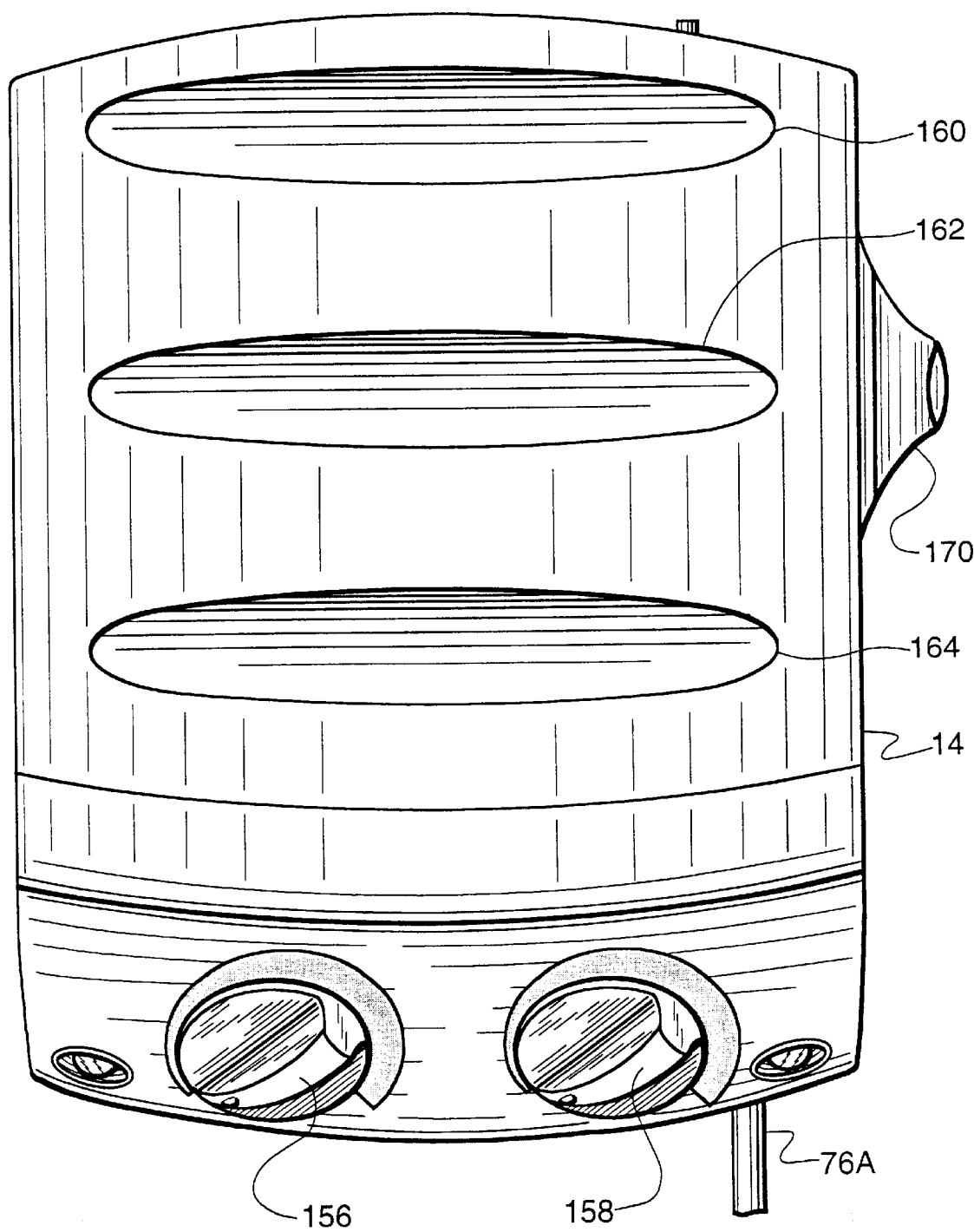
FIG. 10 is a top view of the scaler housing in accordance with the invention shown in FIGS. 10–13.
Figure 11:
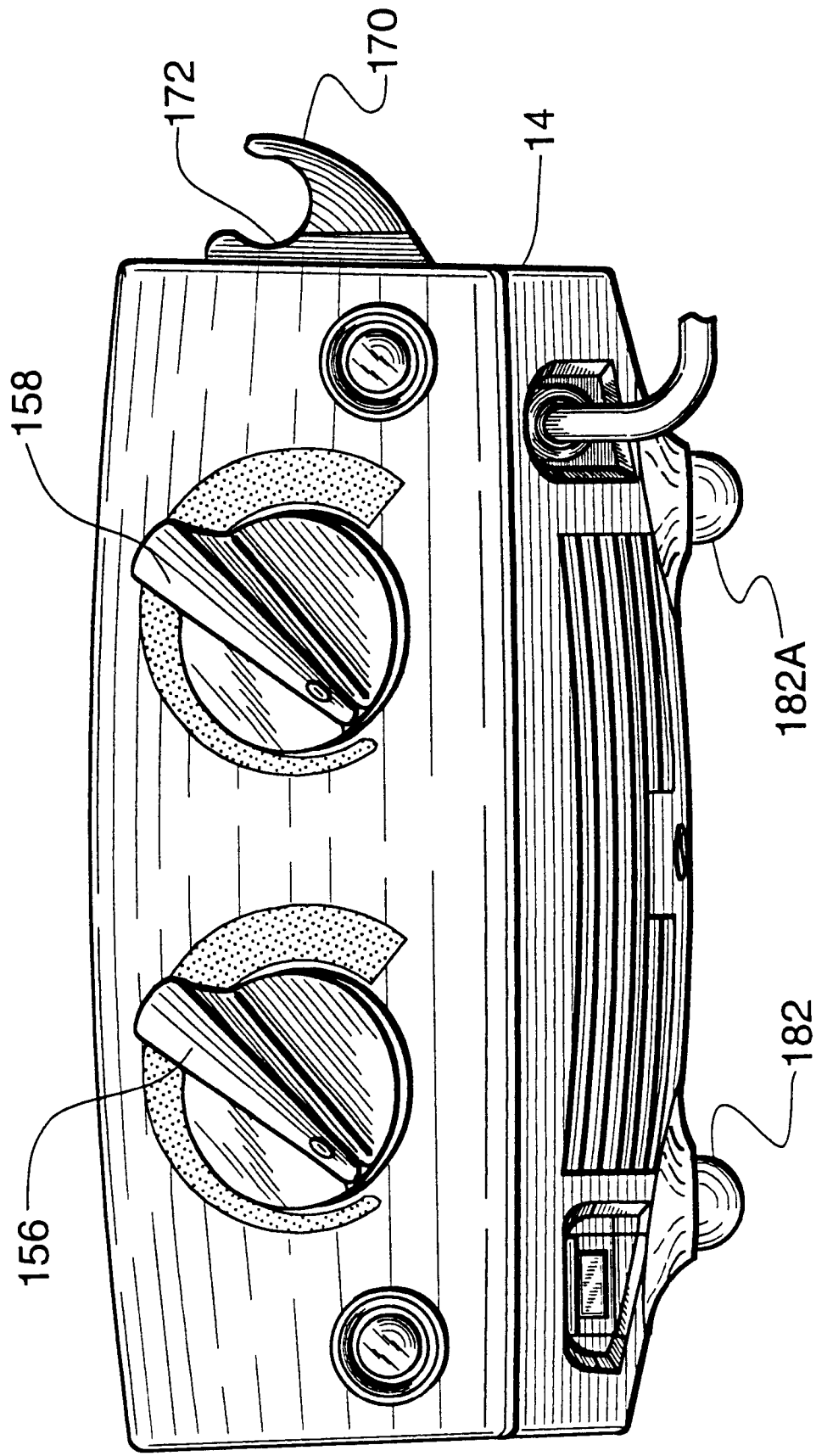
FIG. 11 is a front view of the scaler housing shown in FIGS. 10–13.
Figure 12:
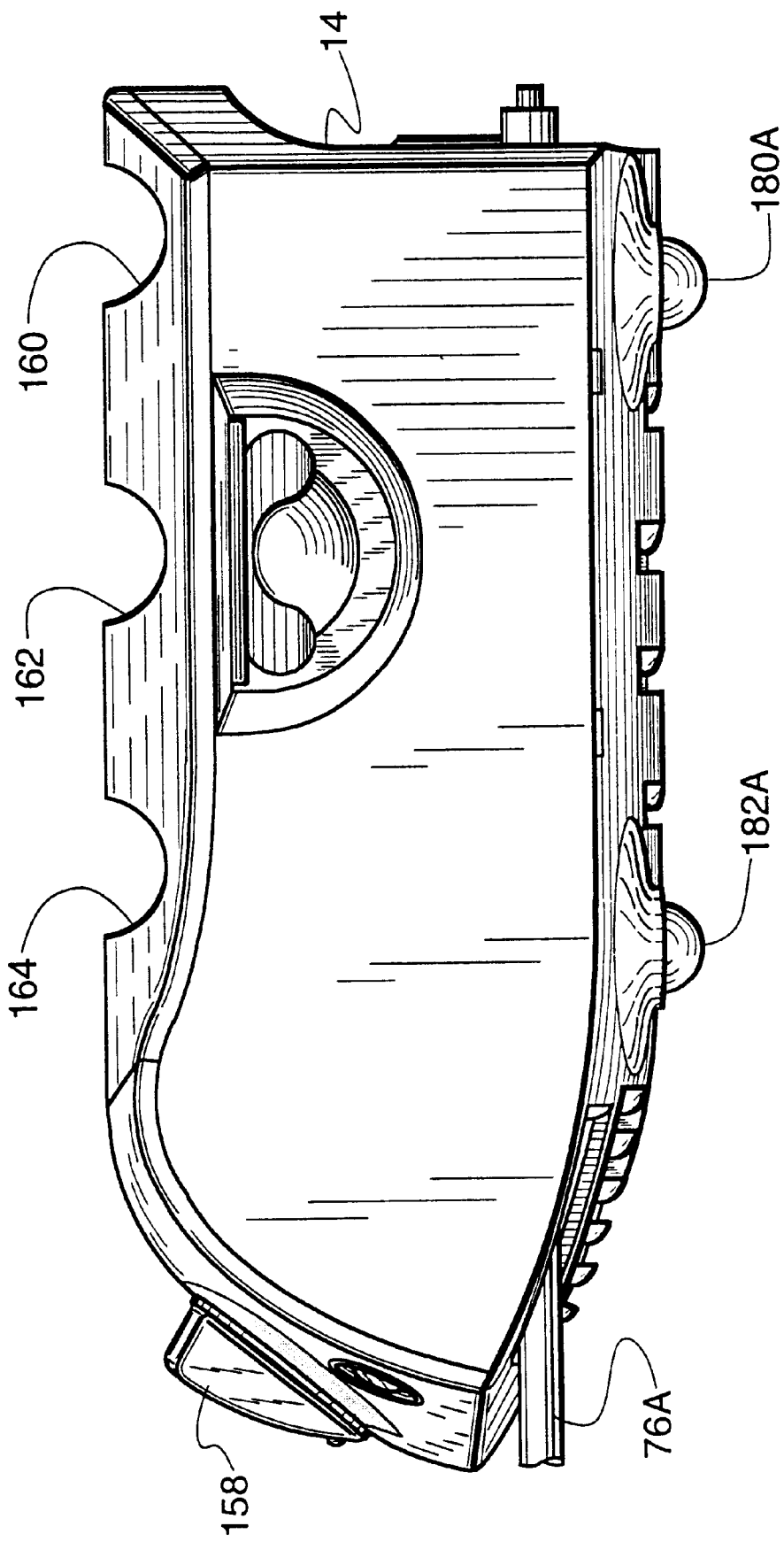
FIG. 12 is a side view of the scaler housing shown in FIGS. 10–13.
Figure 13:
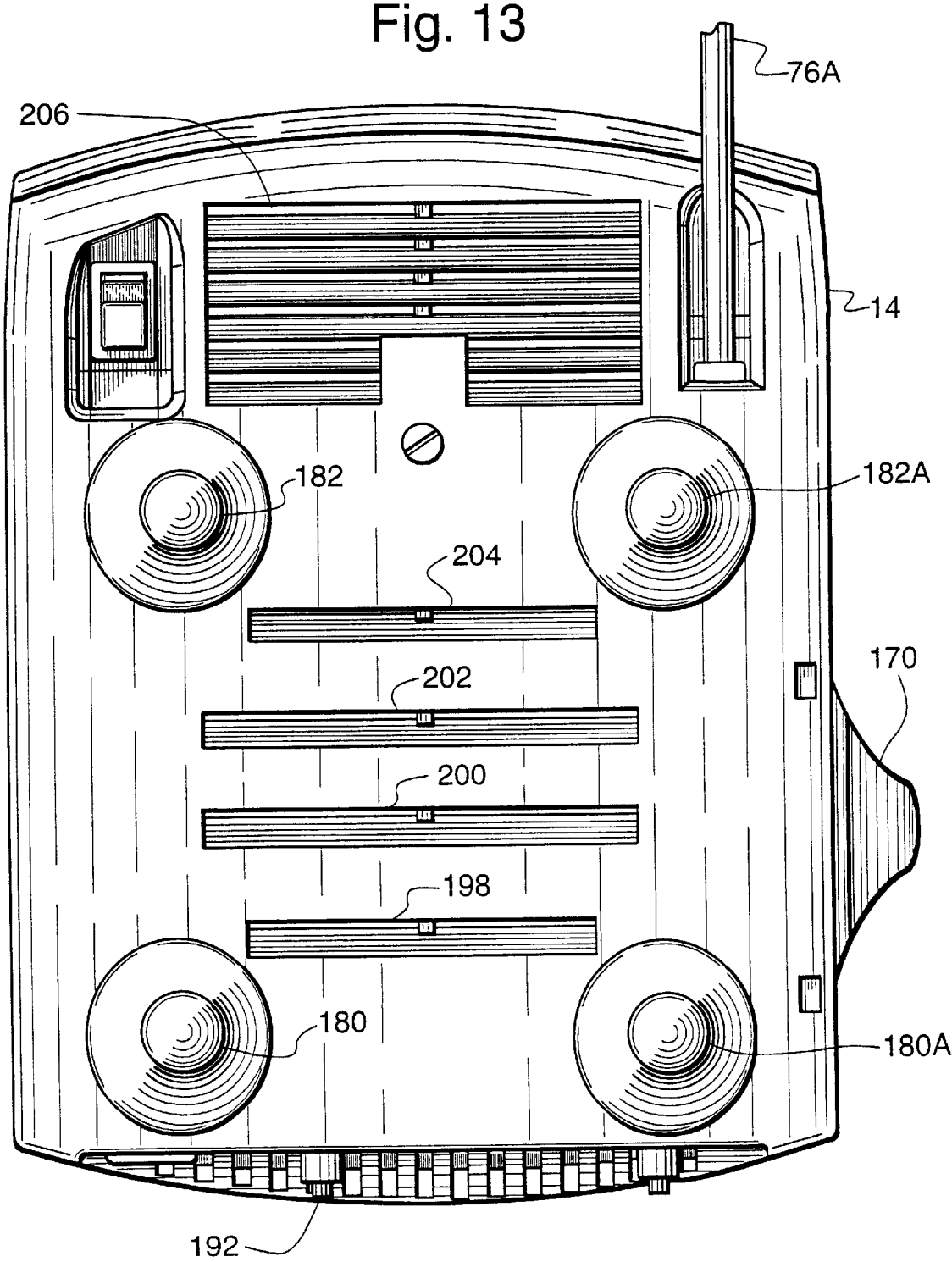
FIG. 13 is a bottom view of the scaler housing shown in FIGS. 10–13.

When lid 102 is in closed position, caps 41 and 43 are held by lid 102 onto the adjacent fluid connectors 42A and 44A as shown in FIGS. 1A and 7A.

Scaler housing 14 is supported by feet 180, 180A, 182 and 182A.

Vents 198, 200, 202, 204 and 206 in the lower wall of scaler housing 14 allow cooling by convection.

Fluid conduit 24 and electrical conductor 76 are enclosed by flexible plastic conduit 76A.

Conduit 20 connected to connector 22 at one end and at the other end to connector 192.

Foot switch 170A is connected by electrical current conductor 170B to power control 70.

Figure 14A:
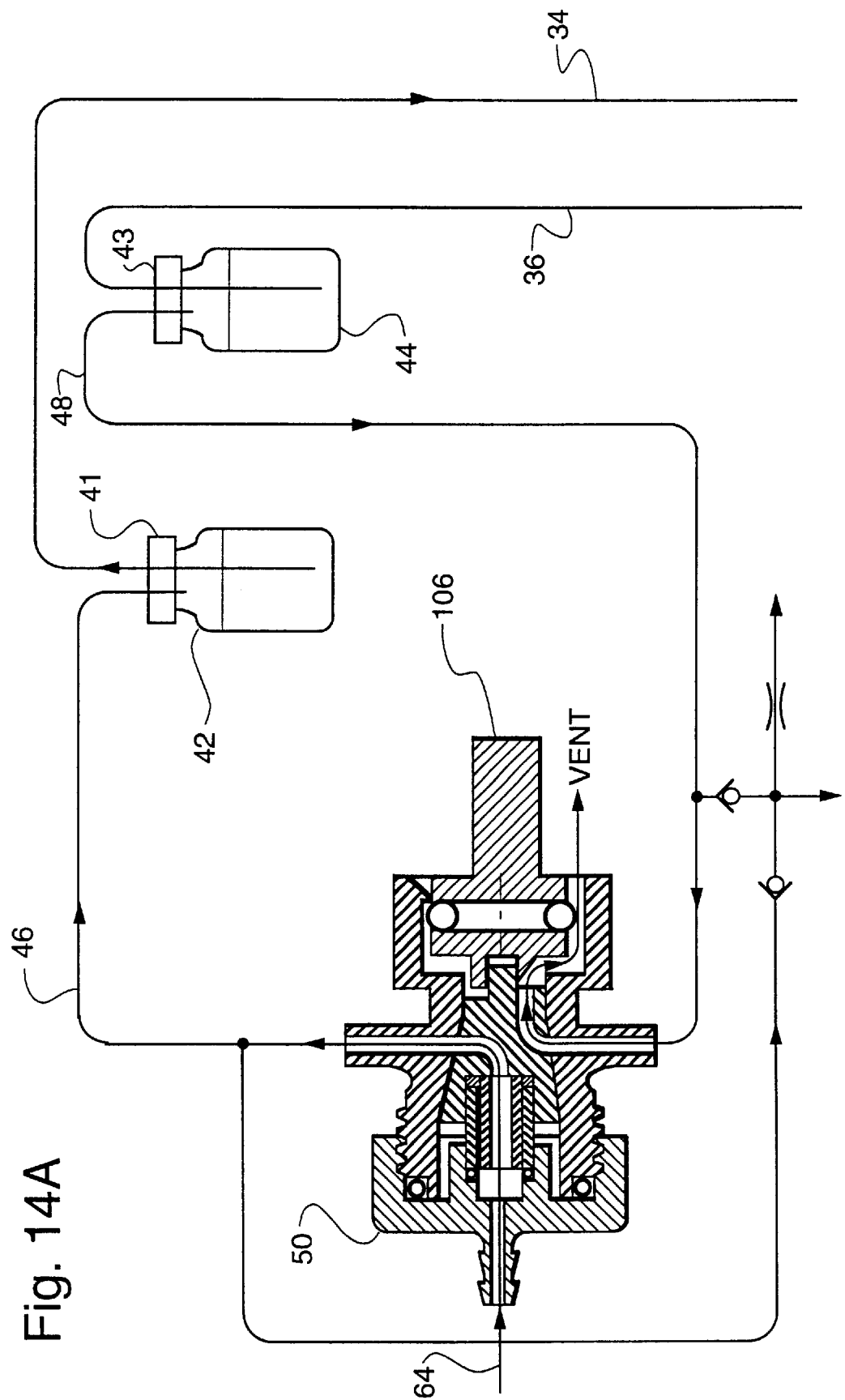
FIGS. 14A, 14B and 14C are schematic diagrams of the air pressure/venting distribution valve (selector valve) in three different positions.
Figure 14B:
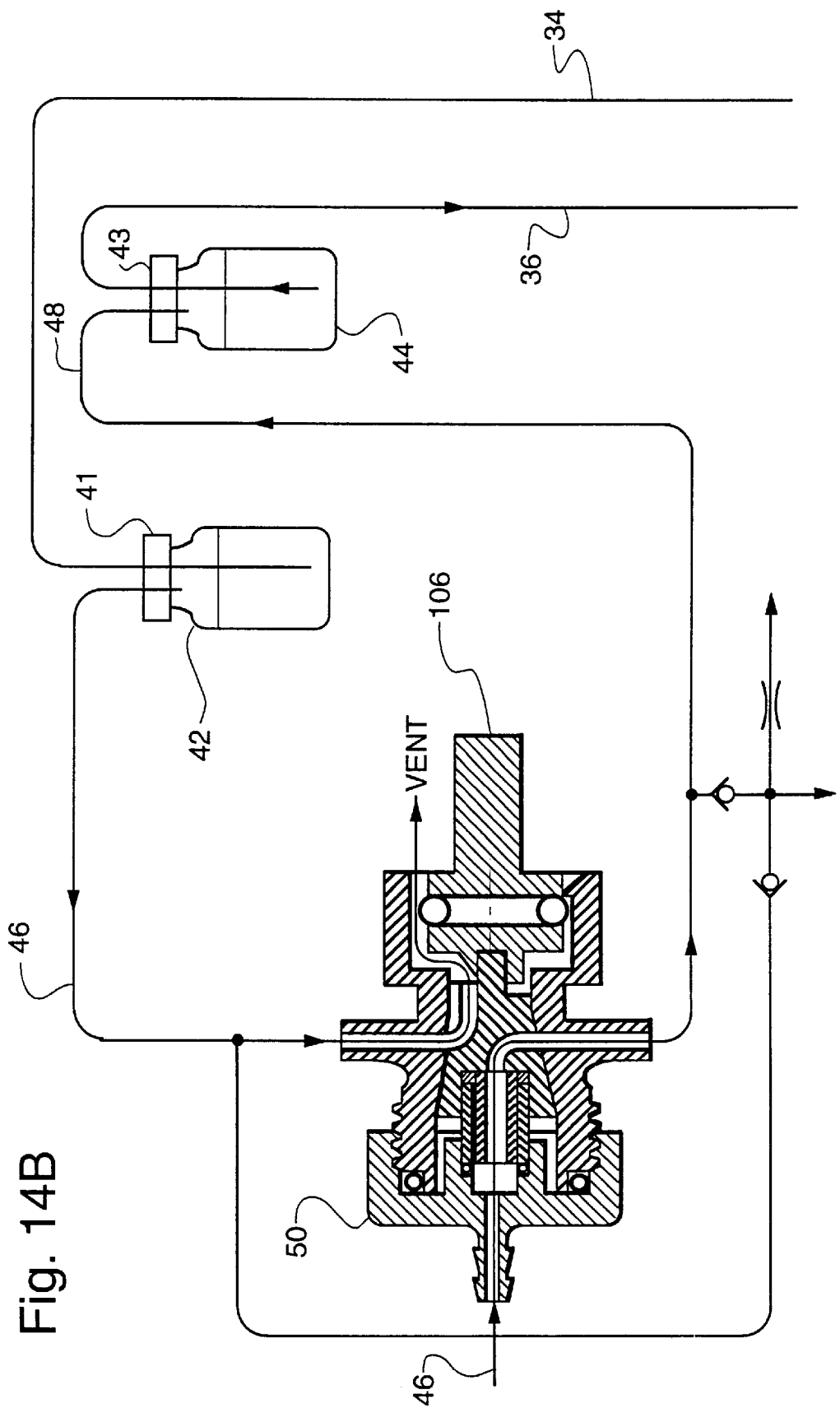
Figure 14C:
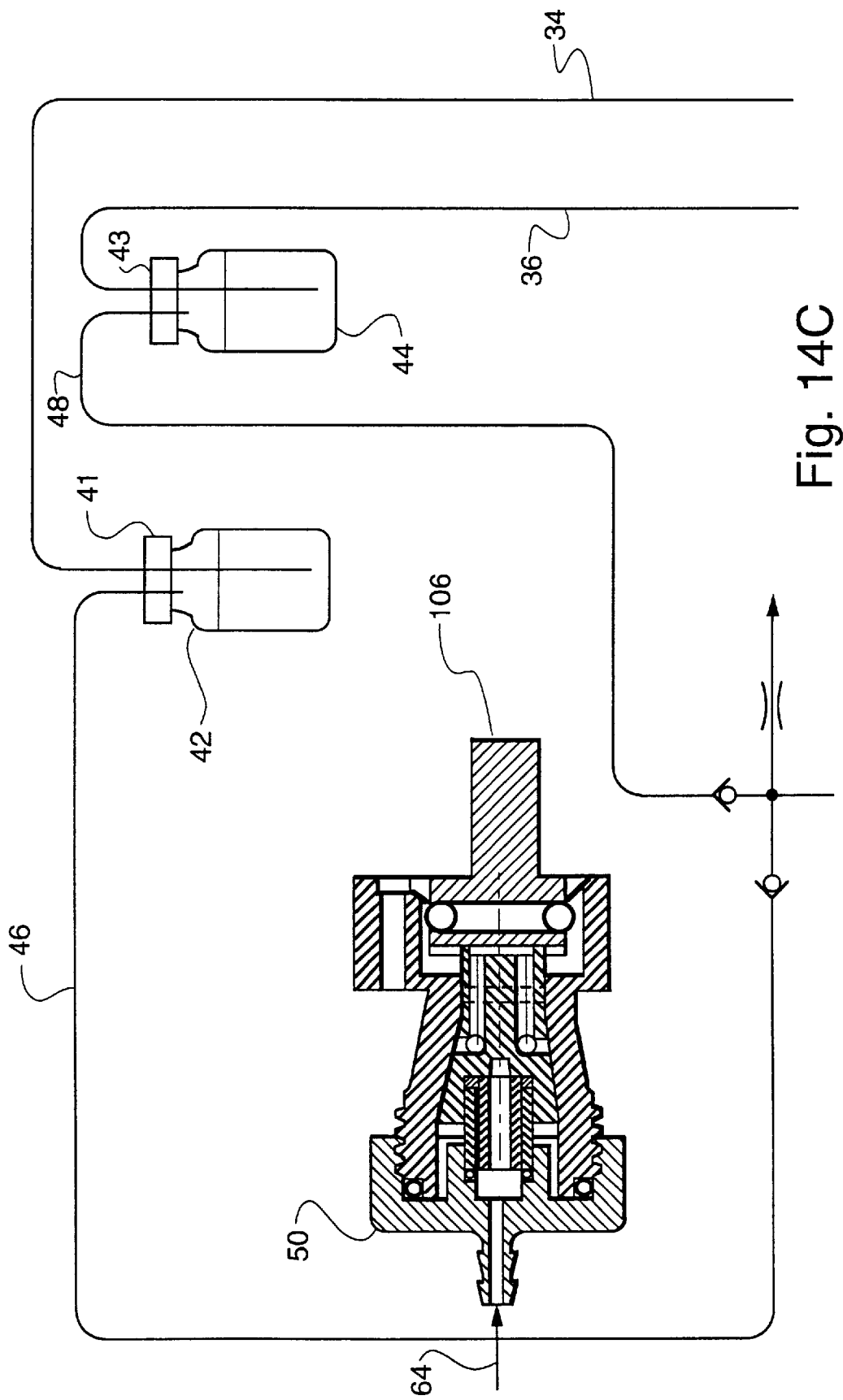
Figure 15:
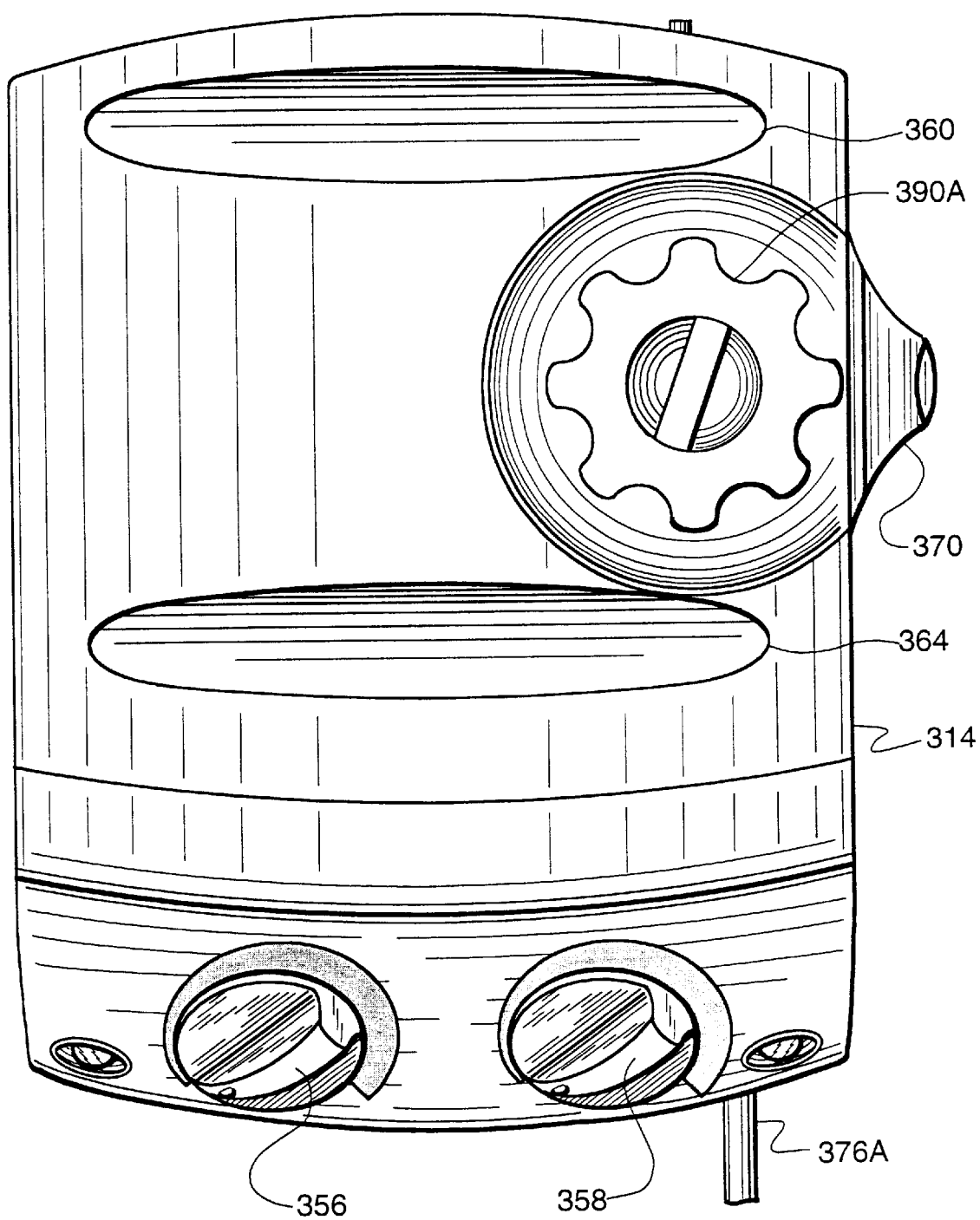
FIG. 15 is a top view of a air polishing housing shown in FIGS. 15–18.
Figure 16:
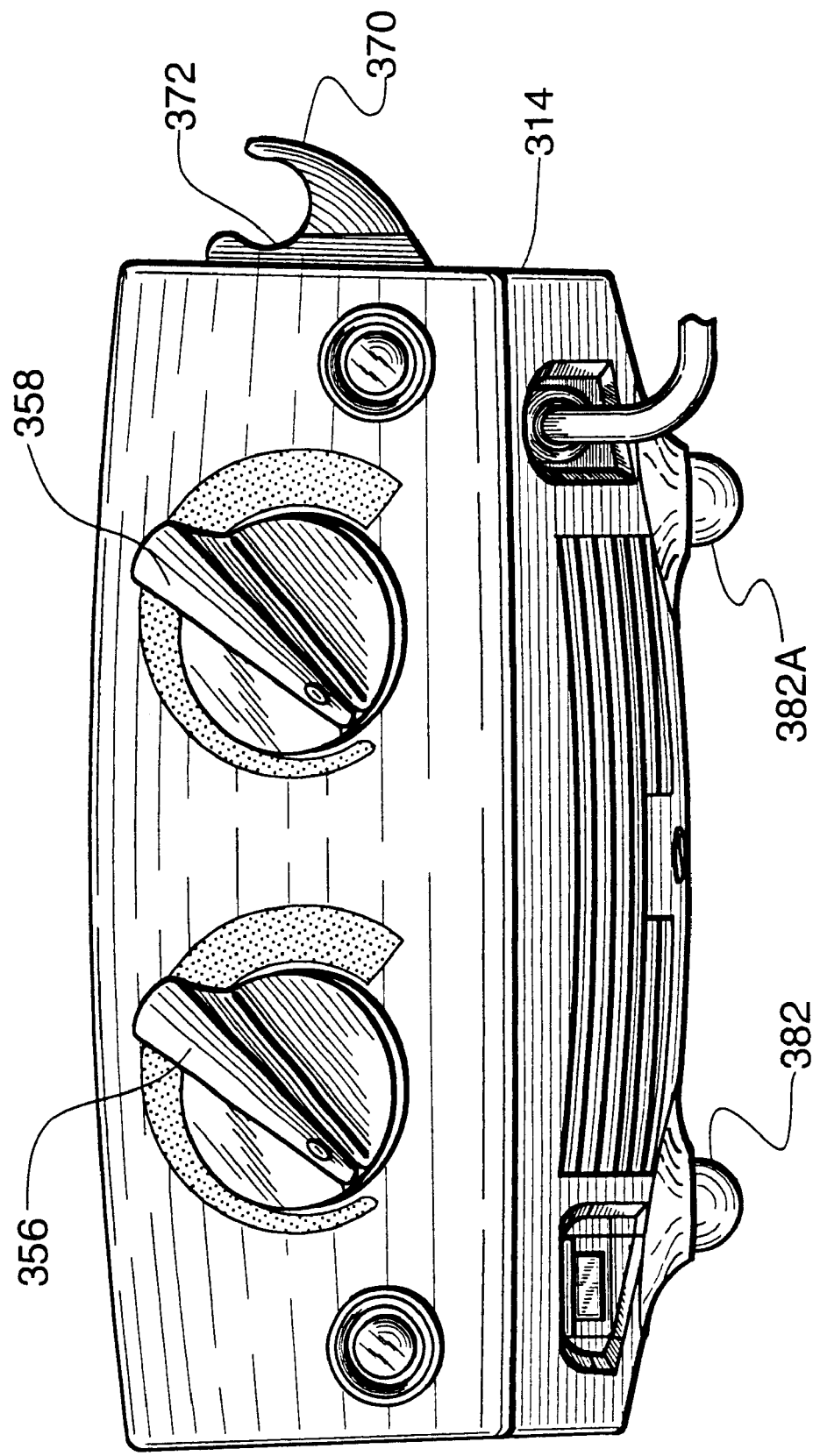
FIG. 16 is a front view of the air polishing housing shown in FIGS. 15–18.
Figure 17:
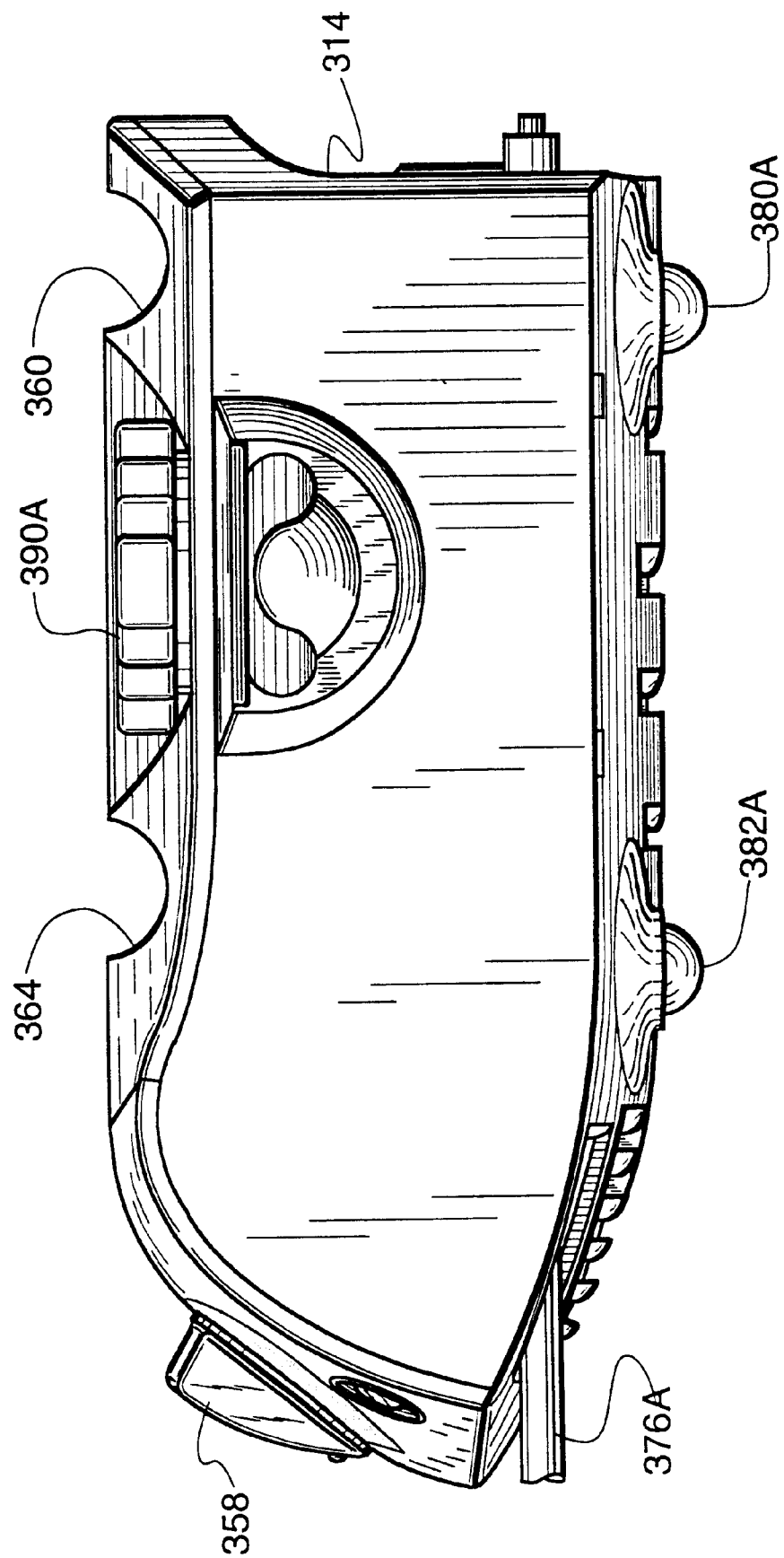
FIG. 17 is a side view of the air polishing housing shown in FIGS. 15–18.
Figure 18:
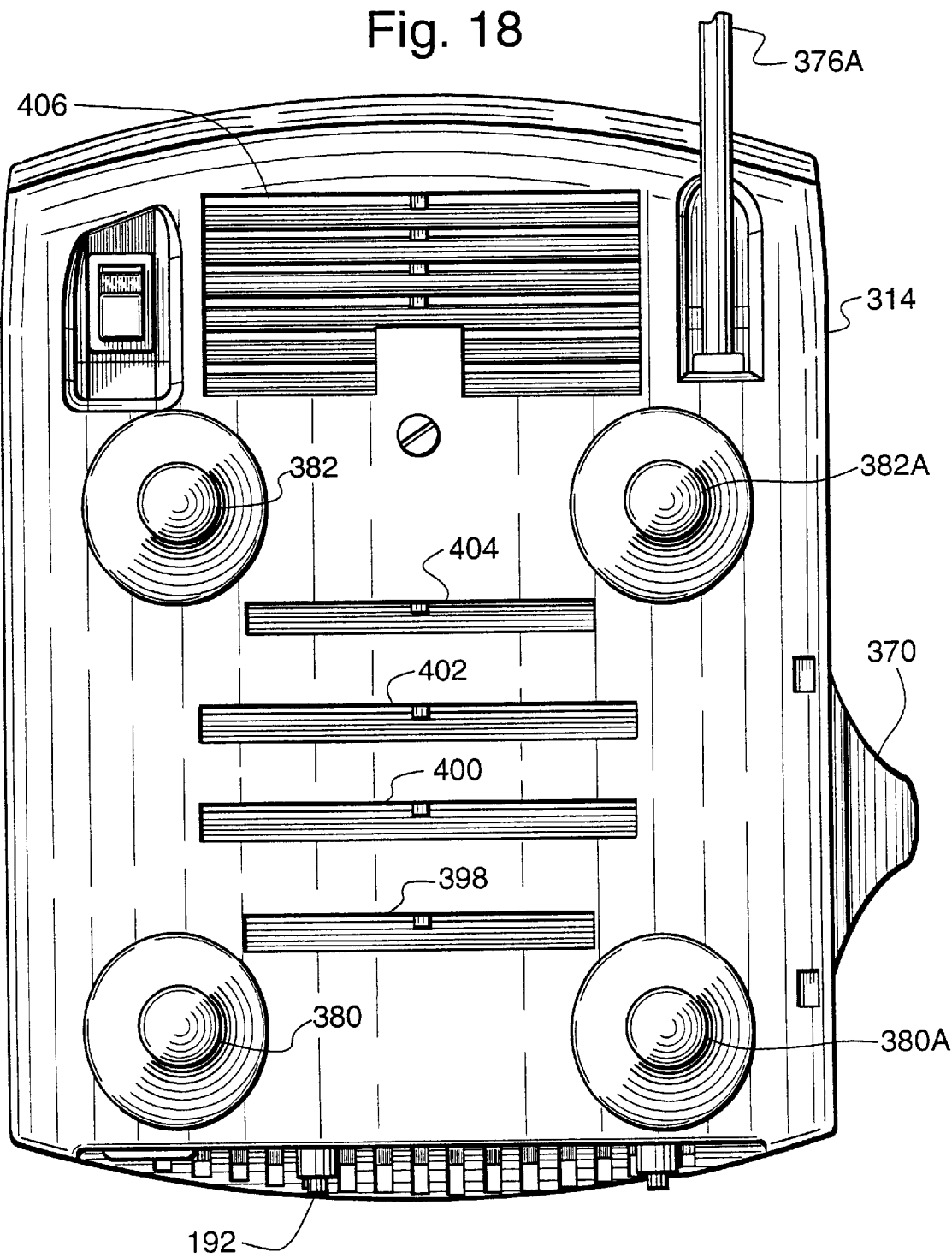
FIG. 18 is a bottom view of the air polishing housing shown in FIGS. 15–18.
Figure 19:
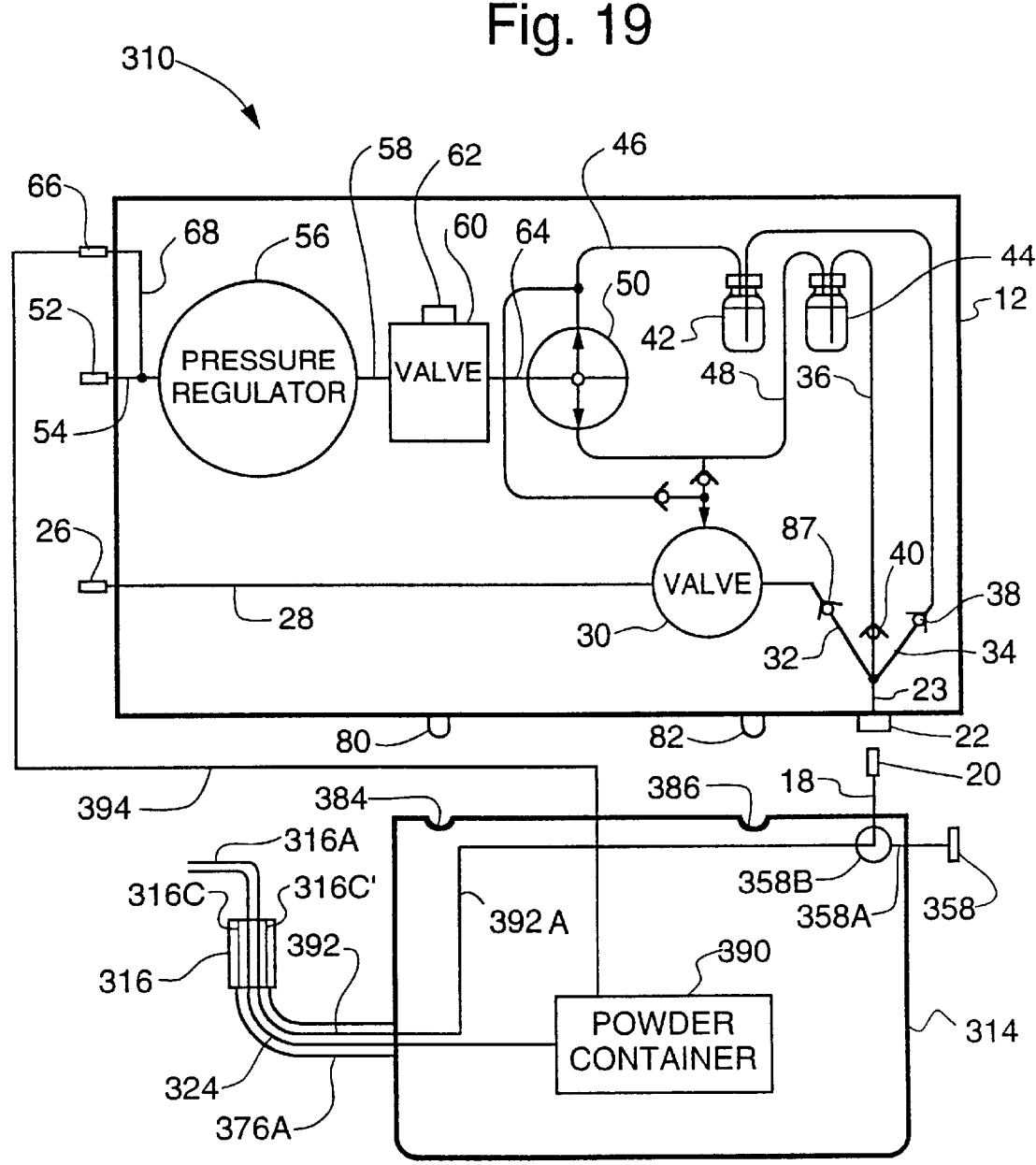
FIG. 19 is a schematic diagram of the stacking dental reservoir shown in FIGS. 1C and 2–9 in use with the air polishing system shown in FIGS. 15–18.
Figure 20:
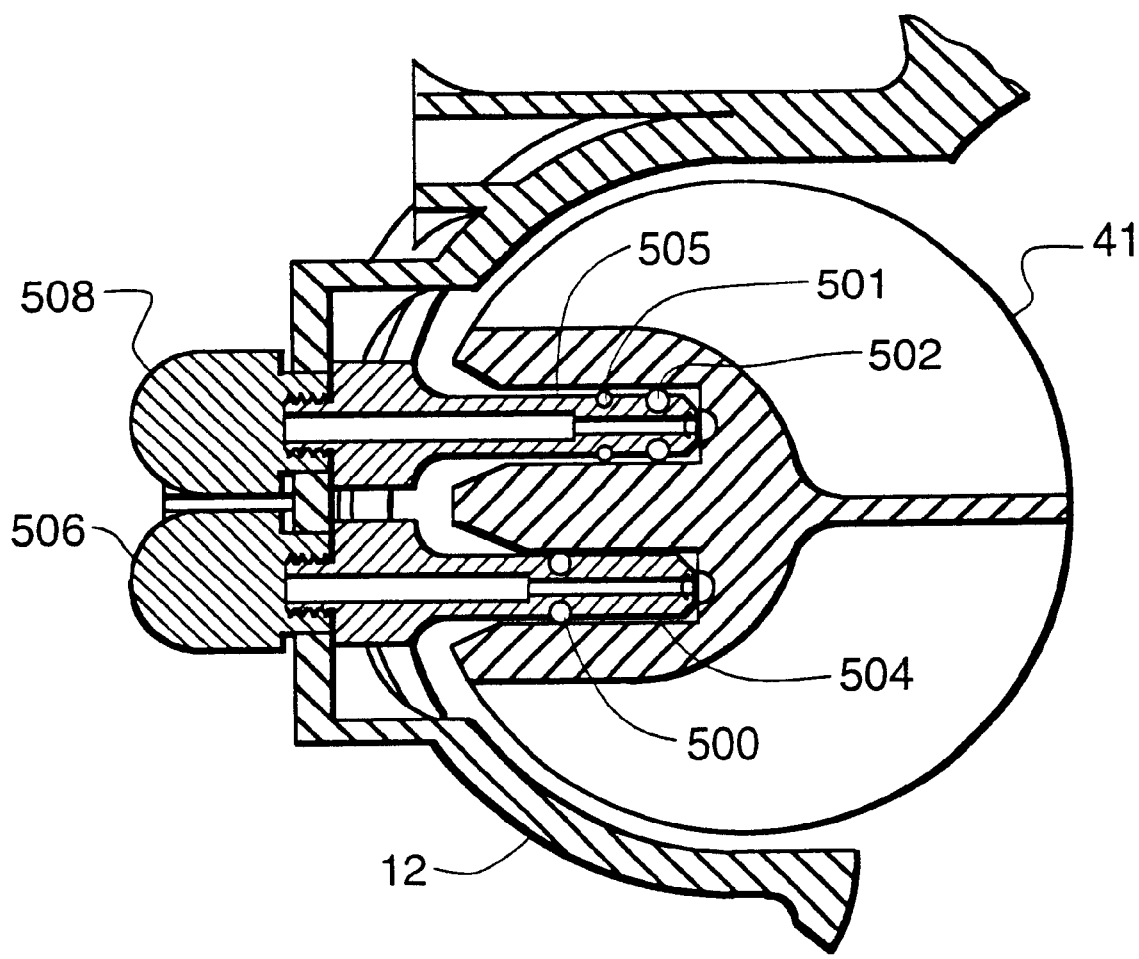
FIG. 20 is a schematic diagram of a partial cross-sectional top view of a reservoir housing showing a cap for a container.

As shown in FIGS. 14, 14A, 14B and 14C valve 50 is rotated to three different positions by turning knob 106. As shown in FIG. 14A by turning valve 50 to the position shown air entering valve 50 through line 64 leaves valve 50 through line 56 to pressurize container 42 causing fluid to flow from container 42 through line 34. As shown in FIG. 14B by positioning valve 50 in the position shown, air enters valve 50 through line 46 and leave valve 50 through line 48. Air in line 48 pressurizes container 44 causing fluid from container 44 to flow through line 36. As shown in FIG. 14C by positioning valve 50 as shown, neither container 42 nor container 44 is pressurized, and fluid does not flow from either container in this position of valve 50. Rather in the position of valve 50 shown in FIG. 14C, air pressure is not supplied to valve 30 and existing air pressure is reduced by a bleed port, opening air pilot valve 30 allowing fluid to flow through line 28 to line 32, as shown in FIG. 14.

With more particular reference to FIGS. 15–19, it is seen that air polishing housing 314 is connected to polishing handpiece 316. Air polishing base housing 314 has grooves 360 and 364 in the upper face thereof. Feet 80 and 82 of reservoir housing are positioned in grooves 360 and 364 of the upper face of the air polishing housing when the reservoir base housing 314 is in stacked position on the air polishing housing. Outer container 390 has container cap 390A. Powder container 390 is connected through a conduit 394 to coupler 66 to provide air pressure in powder container 390. Powder from powder container 390 is conveyed under pressure through conduit 392 to handpiece 316. Fluid is conveyed through line 18 to air polishing base housing 314. Fluid is conveyed from air polishing 314 through conduit 324 to handpiece 316. Handpiece 316 is provided with a mixing tip 316A which sprays liquid from an outer concentric orifice and sprays powder from an inner-circular orifice. Thus, it provides an annulus of liquid around a circular stream of powder which mixes in the spray prior to polishing the tooth surface. Conduits 392 and 324 are enclosed by flexible plastic cover 376A. Polishing base is supported by feet 380, 382, 380A and 382A. The lower face of air polishing base housing 314 has vent 398, 400, 402, 404 and 406. Handpiece 316 is adapted to be held by holder 370. Knobs 356 and 358 are connected to a variable power control unit, and a fluid flow control valve respectively. Knob 358 is connected by valve stem 358A to fluid flow control valve 358B.

Upon disengaging reservoir cap 41 from housing 12, O-ring 500 unseals relieving any residual air pressure in container 42, with further outward movement of the cap, O-ring 501 is unseated, and a vent hole is exposed to atmospheric pressure, thereby allowing any fluid remaining in the passageway of the coupler to move back into container 42 avoiding spillage during final withdrawal of cap 41 and container 42 from housing 12 past O-ring 501. Connectors (or couplings) 504 and 505 are connected in fluid flow communication with connectors (or couplings) 506 and 508 respectively. Connector 506 is connected in fluid flow communication with conduit 46. Connector 508 is connected in fluid flow communication with conduit 34.

Figure 1B:
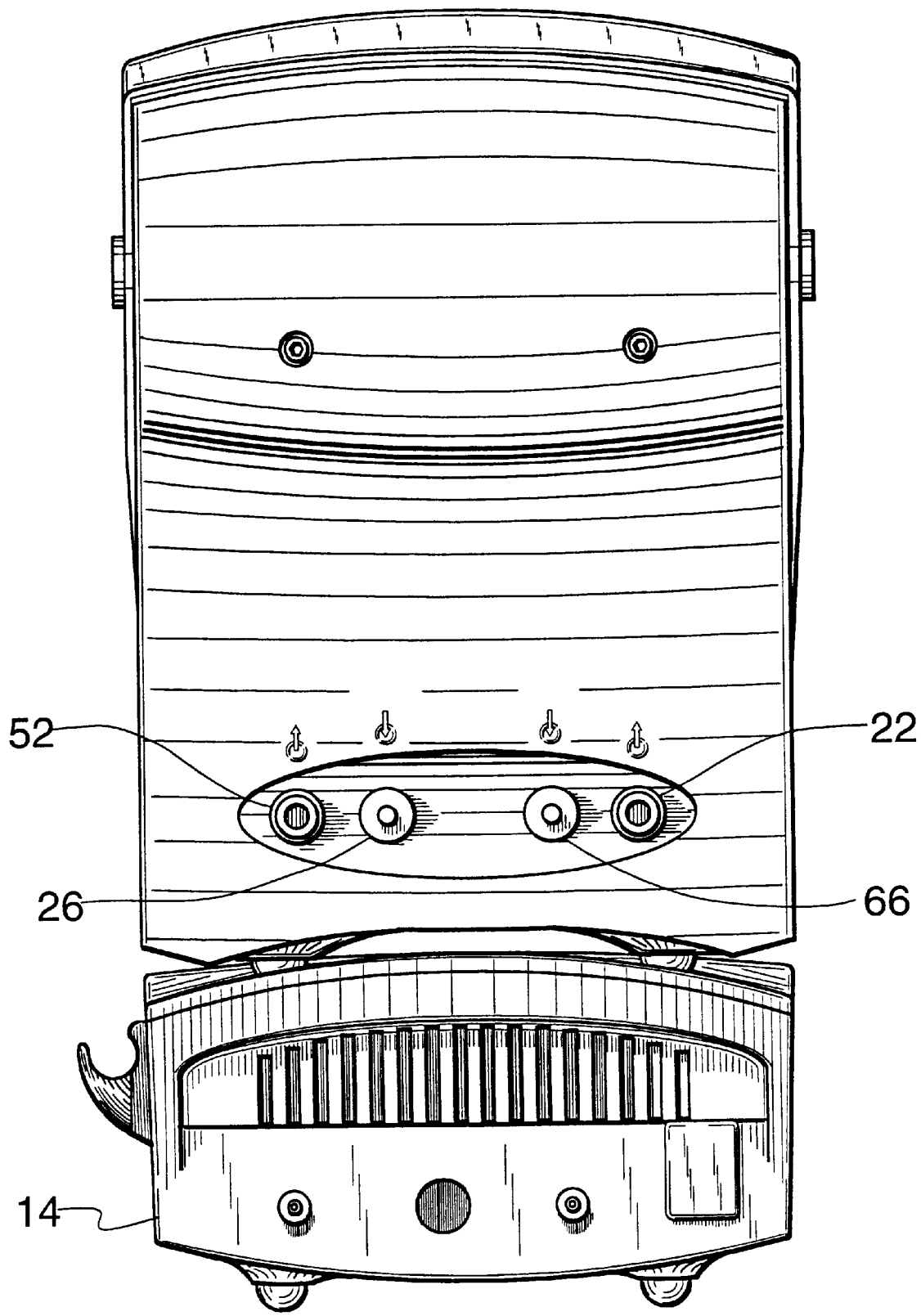
FIG. 1B is a rear view of the stackable reservoir housing stacked upon a scaler housing shown in FIGS. 1 and 1A.
Figure 1C:
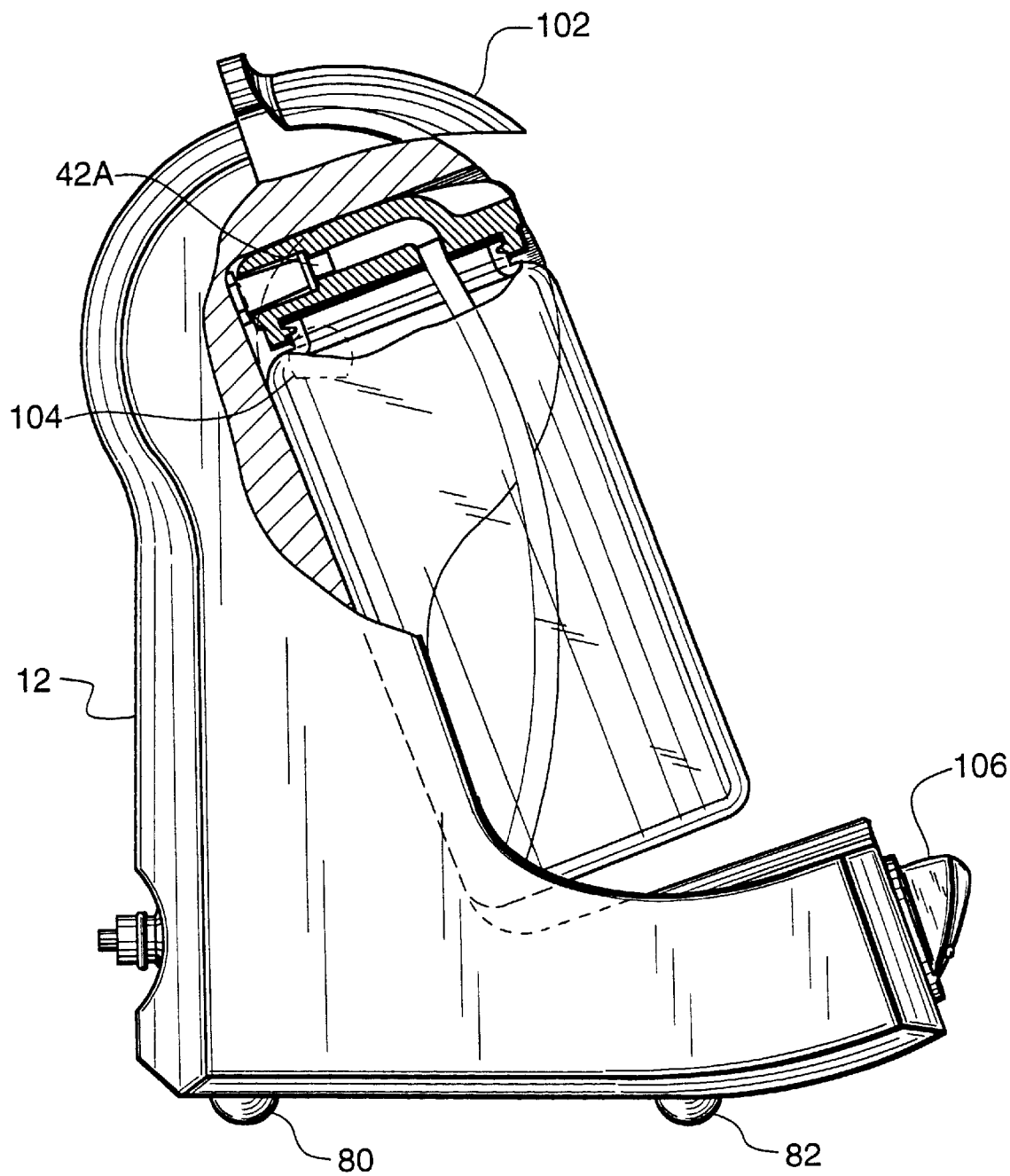
FIG. 1C is a side view of the stackable reservoir housing in accordance with the invention shown in FIGS. 1–9 with the lid partially cut away.
Figure 2:
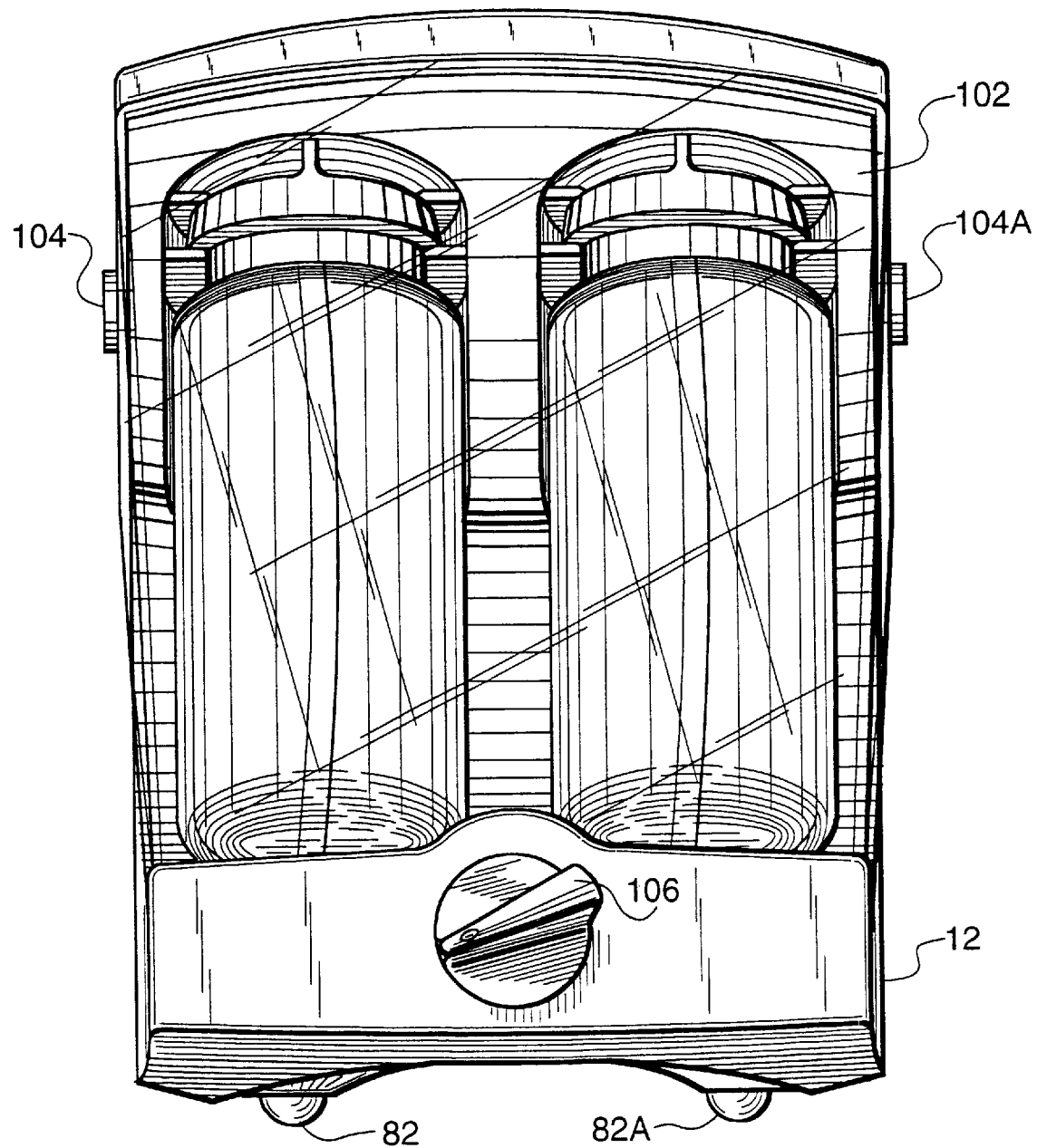
FIG. 2 is a front view of the stackable reservoir housing shown in FIGS. 1–9.
Figure 3:
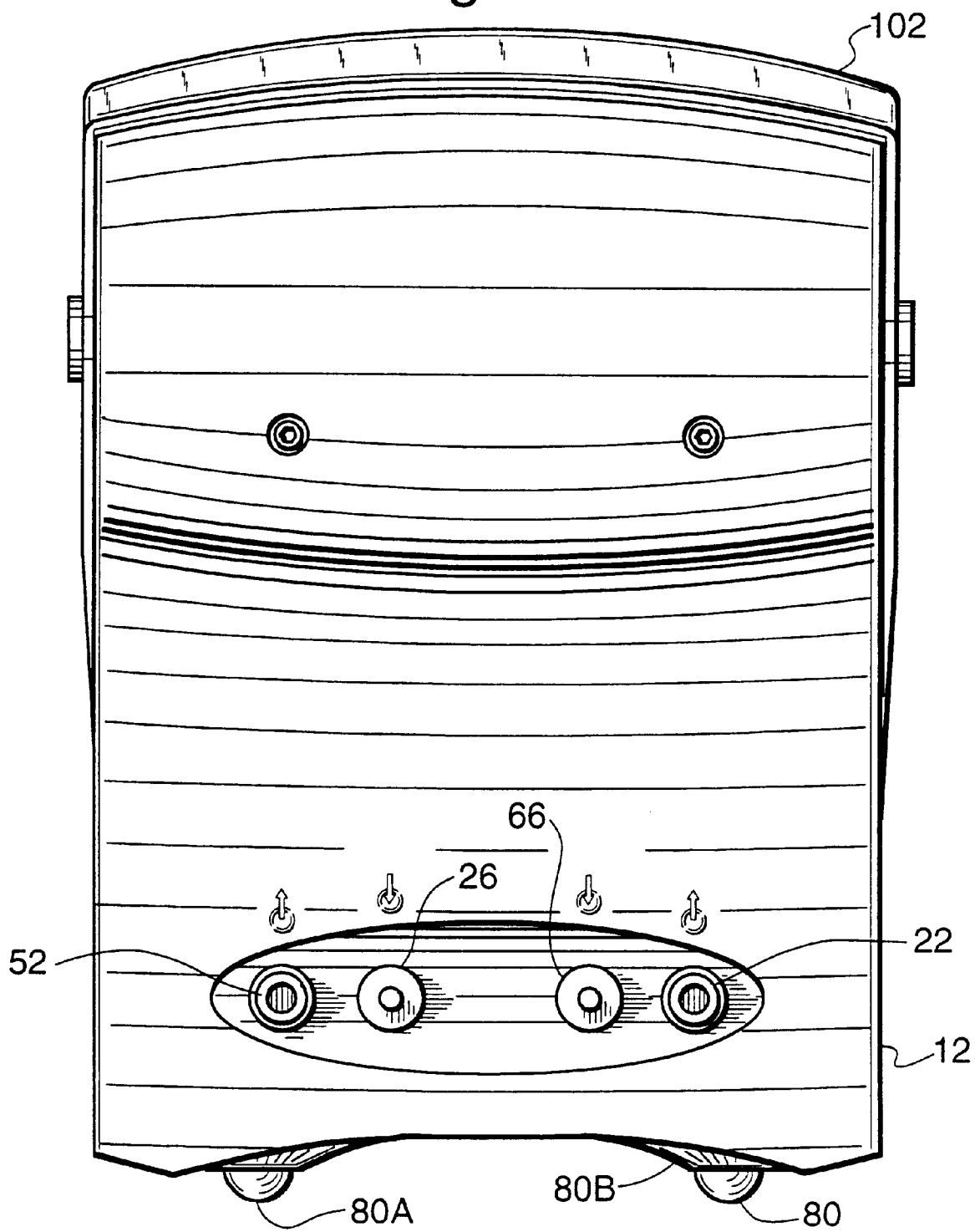
FIG. 3 is a rear view of the stackable reservoir housing shown in FIGS. 1–9.
Figure 4:
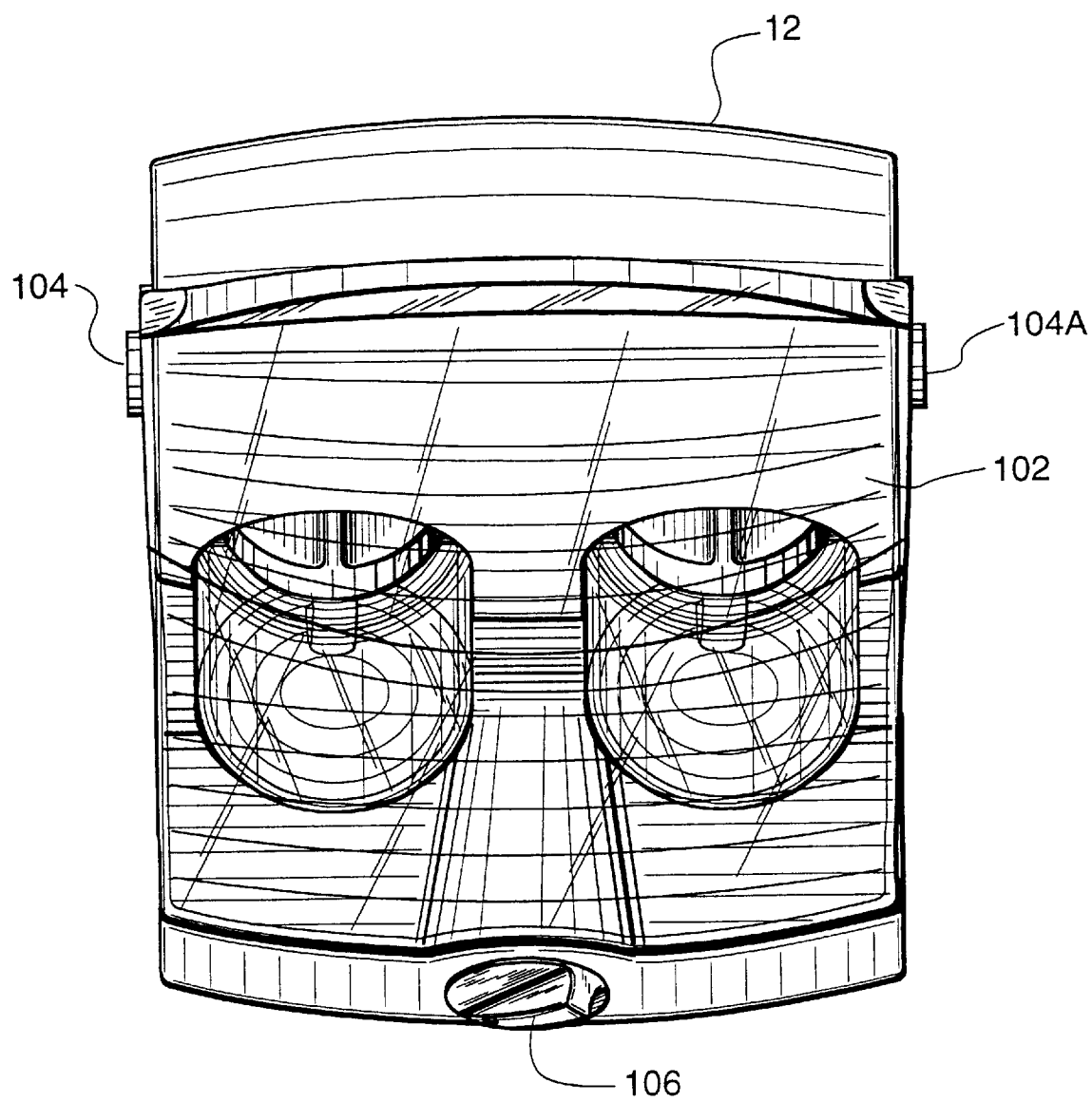
FIG. 4 is a top view of the stackable reservoir housing shown in FIGS. 1–9.
Figure 5:
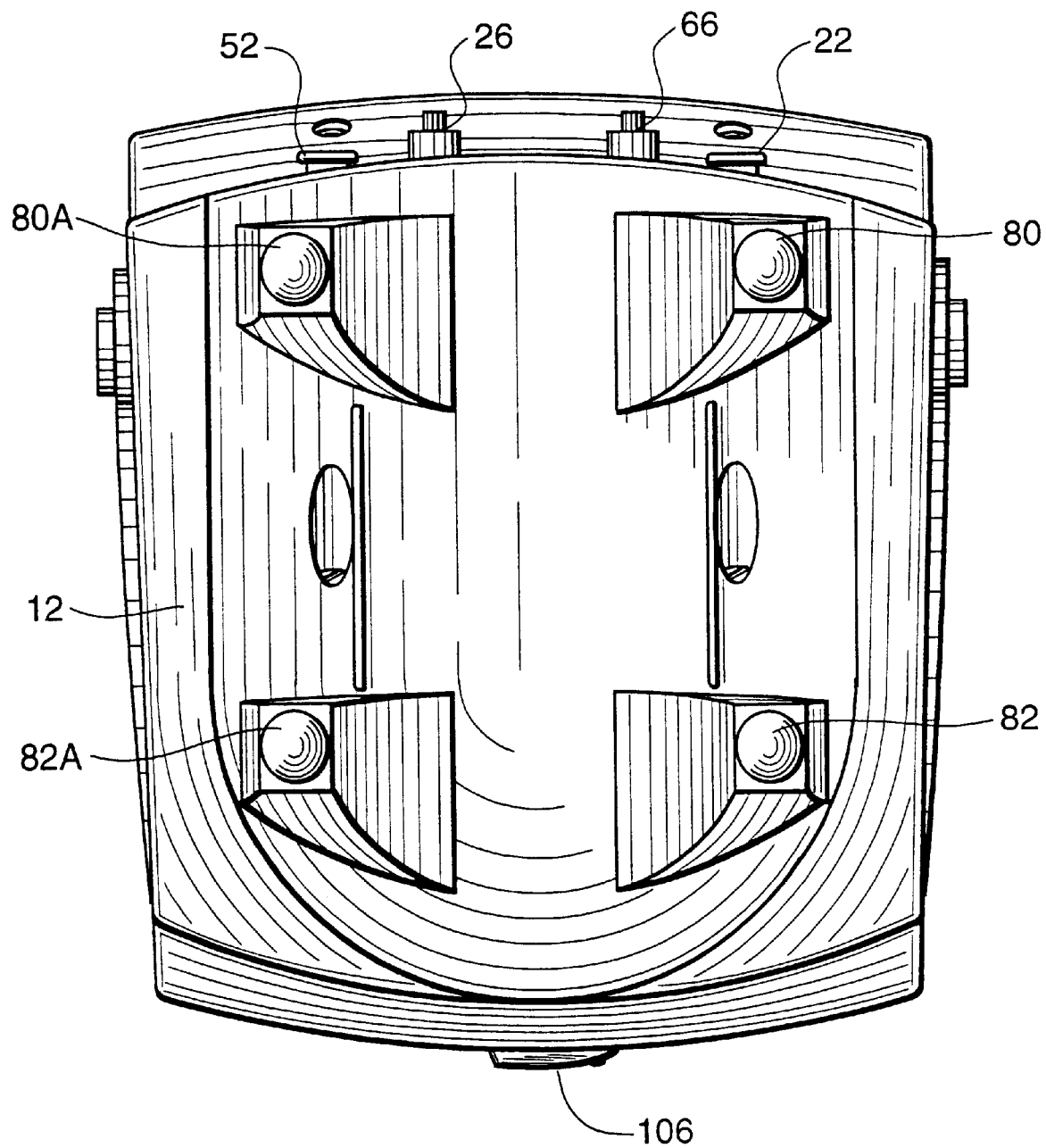
FIG. 5 is a bottom view of a stackable reservoir housing shown in FIGS. 1–9.
Figure 6:
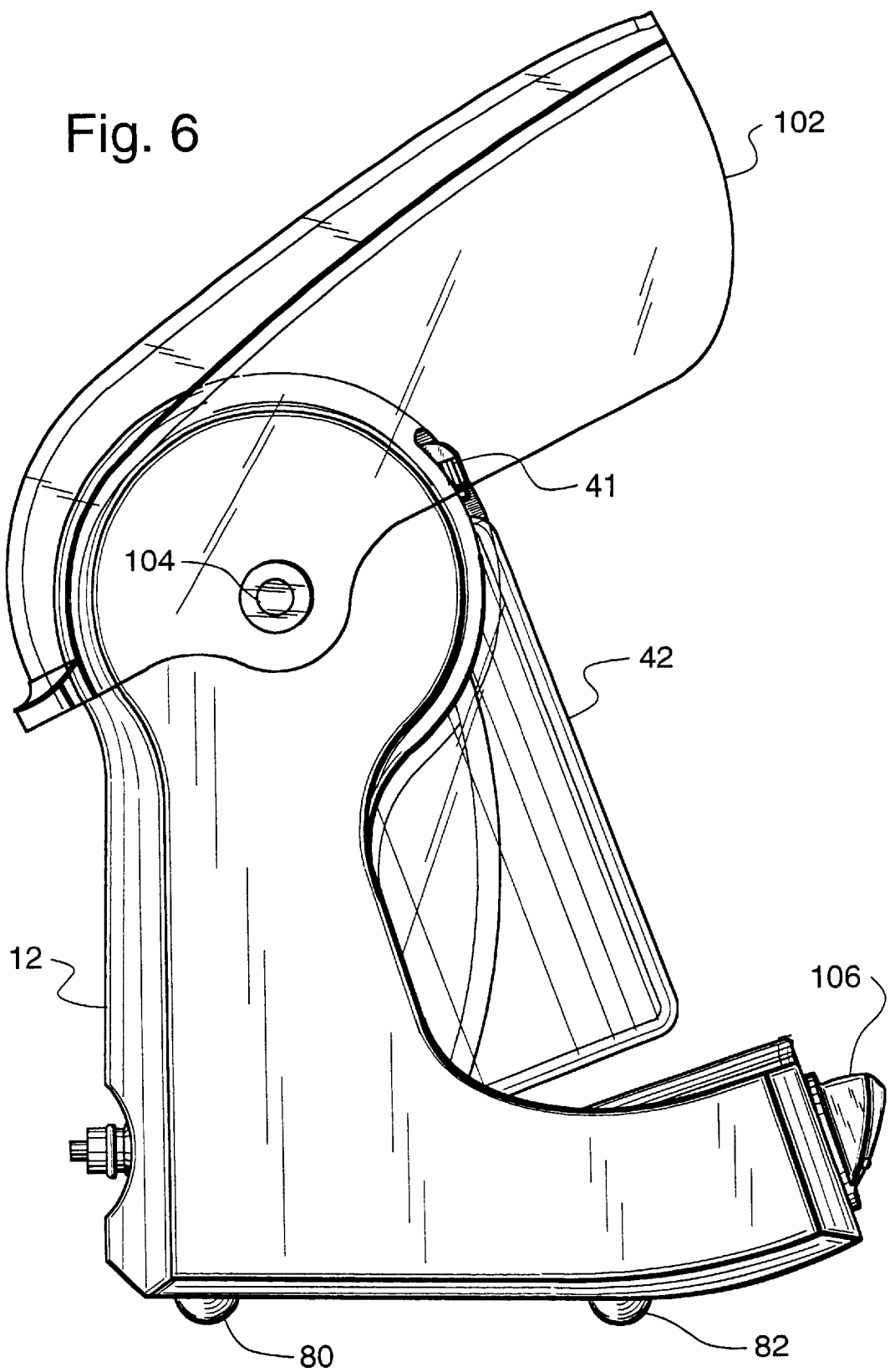
FIG. 6 is a side view of a stackable reservoir housing shown in FIGS. 1–9 with its lid in open position.

As shown in FIGS. 1, 1A and 1B reservoir housing 12 has a height from the rounded top end to the bottom end, a width from side to side (the sides are parallel), a lower depth from front to back at the bottom end, a middle depth from front to back at the midpoint of the height and an upper depth from front to back at the center of the rounded top end. The reservoir housing height is greater than the width. The reservoir housing lower depth is greater than the upper depth. The reservoir housing upper depth is greater than the middle depth.

It will be apparent to those skilled in the art that various modifications and changes may be made in the practice and use of the present invention without departing from the scope thereof as set forth in the following claims.

What is claimed is:

1. A stacking system comprising:
   a reservoir housing,
   a base housing and
   an ultrasonic dental handpiece having an electrically conducting coil,
   said reservoir housing supporting a readily removable first container said reservoir housing having feet,
   said reservoir housing having a base end connected to said feet,
   said reservoir housing being supported by and positioned above said base housing, said base housing having an upper face, said upper face having grooves, said feet being positioned in said grooves, said first container being in fluid flow communication with said handpiece.

2. The system of claim 1 wherein said first container is connected through conduit means to a valve.

3. The system of claim 2 wherein said valve is connected through a conduit to a source of air at a pressure of at least 35 psi.

4. The system of claim 2 wherein said reservoir housing supports a second readily removable container, said second container being connected through a conduit to said valve.

5. The system of claim 1 wherein said base housing encloses a base housing conduit.

6. The system of claim 5 wherein said base housing conduit is connected to a base housing connector, said base housing connector being connected to said base connecting conduit.

7. The system of claim 1 wherein said first container encloses a fluid, said fluid comprising medicament.

8. The system of claim 7 wherein said reservoir housing further comprises a cover and said first container is enclosed by said reservoir housing when said cover is in closed position.

9. The system of claim 1 wherein said base housing encloses a power control circuit, said power control circuit is connected to said coil in said handpiece,
   said reservoir housing has a cover consisting essentially of clear transparent plastic,
   said first container has a first container fluid flow connector, said reservoir housing has a first reservoir fluid flow connector, said first reservoir housing connector engages said first container connector,
   said reservoir housing has a base end and a hinge end, said base end is connected to said feet, said hinge end is substantially opposite to said base end, said hinge end supporting a hinge, said hinge end is connected to said first and second housing fluid flow connector,
   said cover is connected to said hinge, said cover is positioned against said first container to prevent movement of said first container whereby said first container connector is held in said first reservoir connector, while said cover is in closed position.

10. A method of using a dental scaler comprising:
    providing a stacking system a reservoir housing, having a base housing and an ultrasonic dental handpiece having an electrically conducting coil and a scaling tip, said reservoir housing supporting a readily removable first container said reservoir housing having feet, said reservoir housing having a base end connected to said feet, said reservoir housing being supported by and positioned above said base housing, said base housing having an upper face, said upper face having grooves, said feet being positioned in said grooves, said first container being in fluid flow communication with said handpiece, and
    scaling a tooth with said tip.

11. A reservoir system comprising:

a reservoir housing, a cover consisting essentially of clear transparent plastic, said reservoir housing supporting a first and a second readily removable container, each said container being in fluid flow communication with a source of pressurized air, said reservoir housing having a rounded top end supporting a hinge, said cover having a rounded end and an opposite end, said cover rounded end being connected to said hinge, said cover being pivotable between a closed position and an open position with said opposite end of said cover above the reservoir housing allowing for removal of said first and second container, said cover in closed position preventing said containers from moving sufficiently, said reservoir housing having a height, a width, a lower depth and an upper depth, said reservoir housing height being greater than said reservoir housing width, said reservoir housing lower depth being greater than said reservoir housing upper depth.

12. The system of claim 11 wherein said reservoir housing has a middle depth and said reservoir housing upper depth is greater than said reservoir housing middle depth.

13. The system of claim 11 further comprising a first cap connected to said first container and a second cap connected to said second container, a first and second conduit, said first conduit being enclosed by said reservoir housing and connected in fluid flow communication through said first cap to said first container, said second conduit being enclosed by said reservoir housing and connected in fluid flow communication through said second cap to said second container.

14. The system of claim 13 further comprising a first coupler and a base housing, said base housing supporting a second coupler, and wherein said first coupler is connected in fluid flow communication to said second coupler, said first conduit is connected in fluid flow communication to said first coupler, said second conduit is connected in fluid flow communication to said first coupler.

15. The system of claim 14 further comprising an ultrasonic handpiece having a handpiece conduit and wherein said base housing encloses a base conduit said base conduit being connected in fluid flow communication to said handpiece conduit and said base conduit being connected in fluid flow communication to said second coupler.

16. The system of claim 11 wherein said reservoir housing supports a first, a second, a third and a fourth housing fluid flow connector, said first cap has a first and a second cap fluid flow connector, said second cap has a third and a fourth cap fluid flow connector, said first housing fluid flow connector is connected in fluid flow communication to said first cap connector, said second housing fluid flow connector is connected in fluid flow communication to said second cap connector, said third housing connector is connected in fluid flow communication to said third cap connector, and said fourth housing connector is connected in fluid flow communication to said fourth cap connector.

17. A method of using a dental scaler comprising:

providing a dental scaler having a reservoir housing, a base housing and an ultrasonic dental handpiece having an electrically conducting coil and a scaling tip, said reservoir housing, and a cover, said reservoir housing supporting a first and a second readily removable container, said reservoir housing having a rounded top end supporting a hinge, said cover having a rounded end and an opposite end, said cover rounded end being connected to said hinge, said cover being pivotable between a closed position and an open position with said opposite end of said cover above the reservoir housing allowing for removal of said first and second container, said cover in closed position preventing said containers from moving sufficiently, said reservoir housing having a height, a width, a lower depth and an upper depth, said reservoir housing height being greater than said reservoir housing width, said reservoir housing lower depth being greater than said reservoir housing upper depth, said first container being in fluid flow communication with said handpiece, and scaling a tooth with said tip.

* * * * *